(12) United States Patent
Walker et al.

(10) Patent No.: US 7,566,700 B2
(45) Date of Patent: Jul. 28, 2009

(54) MATERIALS AND METHODS FOR TREATMENT OF ALLERGIC DISEASE

(75) Inventors: William Walker, Swansea (GB); Julian Meurglyn Hopkin, Swansea (GB)

(73) Assignee: Allerna Therapeutics Limited (GB)

( * ) Notice: Subject to any disclaimer, the term of this patent is extended or adjusted under 35 U.S.C. 154(b) by 413 days.

(21) Appl. No.: 10/590,680

(22) PCT Filed: Feb. 25, 2005

(86) PCT No.: PCT/GB2005/000721

§ 371 (c)(1),
(2), (4) Date: Aug. 25, 2006

(87) PCT Pub. No.: WO2005/083083

PCT Pub. Date: Sep. 9, 2005

(65) Prior Publication Data

US 2008/0234212 A1  Sep. 25, 2008

(30) Foreign Application Priority Data

Feb. 25, 2004 (GB) ................................ 0404209.9

(51) Int. Cl.
*A61K 31/70* (2006.01)
*C07H 21/04* (2006.01)
*C07H 21/02* (2006.01)
*C12Q 1/68* (2006.01)

(52) U.S. Cl. .............................. 514/44; 435/6; 435/375; 536/23.1; 536/24.1; 536/24.5

(58) Field of Classification Search ........................ None
See application file for complete search history.

(56) References Cited

U.S. PATENT DOCUMENTS

2007/0031844 A1* 2/2007 Khvorova et al. ............... 435/6

FOREIGN PATENT DOCUMENTS

WO    WO 98/40478    9/1998

OTHER PUBLICATIONS

RNAi as a novel asthma therapeutic—Implications for IP development, RNAi & Treatment of Human Disease.
Danahay, H. et al., "The in vitro and in vivo pharmacology of antisense oligonucleotides targeted to murine Stat6," *Inflamm. Res.* 49; 692-699 (2000).
Hill, Sandra, et al., "Homologous Human and Murine Antisense Oligonucleotides Targeting Stat6," *Am. J. Respir. Cell Mol. Biol.*, vol. 21, 728-737 (1999).
New asthma drugs acting on gene expression: Progress in Molecular Pharmacology, *J. Cell. Mol. Med.* vol. 7, No. 4, 475-486 (2003), Popescu et al.
Rippmann, Jorg F. et al., "Gene silencing with STAT6 specific siRNAs blocks eotaxin release in IL-4/TNFα stimulated human epithelial cells," *FEBS Letters* 579, 173-178 (2005).
Arenz, Christoph, et al., "RNA interference: from an ancient mechanism to a state of the art therapeutic application?" *Naturwissenschaften*, 90:345-359 (2003).
Henschel, Andreas, et al., "DEQOR: a web-based tool for the design and quality control of siRNAs," *Nucleic Acids Research*, vol. 32, W113-W120 (2004).
Ichim, Thomas E. et al., "RNA Interference: A Potent Tool for Gene-Specific Therapeutics," *American Journal of Transplantation*, 4:1227-1236 (2004).

* cited by examiner

*Primary Examiner*—Sean R McGarry
(74) *Attorney, Agent, or Firm*—Kohn & Associates

(57) ABSTRACT siRNA molecules are disclosed which target the transcription factor STAT6 and repress the expression of STAT6 mRNA, STAT6 protein and STAT6 function in lung cells. The use of STAT6 specific siRNA molecules in the treatment of allergic diseases of the respiratory tract such as asthma and rhinitis is disclosed.

16 Claims, 19 Drawing Sheets

| DNA sequence encoding mRNA | siRNA Duplex Structure |
|---|---|
| STAT6(1): AAGCAGGAAGAACTCAAGTTT → | 5'-GCAGGAAGAACUCAAGUUUtt-3'<br>3'-ttCGUCCUUCUUGAGUUCAAA-5' |
| [SEQ ID No.15] | [SEQ ID No.1] |
| STAT6(2): AAACAGTACGTTACTAGCCTT → | 5'-ACAGUACGUUACUAGCCUUtt-3'<br>3'-ttUGUCAUGCAAUGAUCGGAA-5' |
| [SEQ ID No.16] | [SEQ ID No.2] |
| STAT6(3): AAGAATCAGTCAACGTGTTGT → | 5'-GAAUCAGUCAACGUGUUGUtt-3'<br>3'-ttCUUAGUCAGUUGCACAACA-5' |
| [SEQ ID No.17] | [SEQ ID No.3] |
| STAT6(4): AAAGCACTGGAGAAATCATCA → | 5'-AGCACUGGAGAAAUCAUCAtt-3'<br>3'-ttUCGUGACCUCUUUAGUAGU-5' |
| [SEQ ID No.18] | [SEQ ID No.4] |

```
LOCUS       NM_003153              3993 bp    mRNA    linear   PRI 27-OCT-2004
DEFINITION  Homo sapiens signal transducer and activator of transcription 6,
            interleukin-4 induced (STAT6), mRNA.
ACCESSION   NM_003153
VERSION     NM_003153.3  GI:23397677
KEYWORDS
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.

COMMENT     REVIEWED REFSEQ: This record has been curated by NCBI staff. The
            reference sequence was derived from BC005823.2 and BQ028928.1.
            On Oct 1, 2002 this sequence version replaced gi:21536302.

Summary: The protein encoded by this gene is a member of the STAT
            family of transcription factors. In response to cytokines and
            growth factors, STAT family members are phosphorylated by the
            receptor associated kinases, and then form homo- or heterodimers
            that translocate to the cell nucleus where they act as
            transcription activators. This protein plays a central role in
            exerting IL4 mediated biological responses. It is found to induce
            the expression of BCL2L1/BCL-X(L), which is responsible for the
            anti-apoptotic activity of IL4. Knockout studies in mice suggested
            the roles of this gene in differentiation of T helper 2 (Th2)
            cells, expression of cell surface markers, and class switch of
            immunoglobulins.
FEATURES             Location/Qualifiers
     source          1..3993
                     /organism="Homo sapiens"
                     /mol_type="mRNA"
                     /db_xref="taxon:9606"
                     /chromosome="12"
                     /map="12q13"
     gene            1..3993
                     /gene="STAT6"
                     /note="synonyms: STAT6B, STAT6C, D12S1644, IL-4-STAT"
                     /db_xref="GeneID:6778"
                     /db_xref="MIM:601512"
     CDS             272..2815
                     /gene="STAT6"
                     /note="STAT, interleukin4-induced; transcription factor
                     IL-4 STAT;
                     go_component: nucleus [goid 0005634] [evidence IEA];
                     go_function: signal transducer activity [goid 0004871]
                     [evidence IEA];
                     go_function: transcription factor activity [goid 0003700]
```

Figure 4

```
                    [evidence TAS] [pmid 10747856];
                    go_process: intracellular signaling cascade [goid 0007242]
                    [evidence IEA];
                    go_process: regulation of transcription from Pol II
                    promoter [goid 0006357] [evidence TAS] [pmid 8810328]"
                    /codon_start=1
                    /product="signal transducer and activator of transcription
                    6"
                    /protein_id="NP_003144.3"
                    /db_xref="GI:23397678"
                    /db_xref="GeneID:6778"
                    /db_xref="MIM:601512"
```

/translation="MSLWGLVSKMPPEKVQRLYVDFPQHLRHLLGDWLESQPWEFLVG

SDAFCCNLASALLSDTVQHLQASVGEQGEGSTILQHISTLESIYQRDPLKLVATFRQI

LQGEKKAVMEQFRHLPMPFHWKQEELKFKTGLRRLQHRVGEIHLLREALQKGAEAGQV

SLHSLIETPANGTGPSEALAMLLQETTGELEAAKALVLKRIQIWKRQQQLAGNGAPFE

ESLAPLQERCESLVDIYSQLQQEVGAAGGELEPKTRASLTGRLDEVLRTLVTSCFLVE

KQPPQVLKTQTKFQAGVRFLLGLRFLGAPAKPPLVRADMVTEKQARELSVPQGPGAGA

ESTGEIINNTVPLENSIPGNCCSALFKNLLLKKIKRCERKGTESVTEEKCAVLFSASF

TLGPGKLPIQLQALSLPLVVIVHGNQDNNAKATILWDNAFSEMDRVPFVVAERVPWEK

MCETLNLKFMAEVGTNRGLLPEHFLFLAQKIFNDNSLSMEAFQHRSVSWSQFNKEILL

GRGFTFWQWFDGVLDLTKRCLRSYWSDRLIIGFISKQYVTSLLLNEPDGTFLLRFSDS

EIGGITIAHVIRGQDGSPQIENIQPFSAKDLSIRSLGDRIRDLAQLKNLYPKKPKDEA

FRSHYKPEQMGKDGRGYVPATIKMTVERDQPLPTPELQMPTMVPSYDLGMAPDSSMSM

QLGPDMVPQVYPPHSHSIPPYQGLSPEESVNVLSAFQEPHLQMPPSLGQMSLPFDQPH

PQGLLPCQPQEHAVSSPDPLLCSDVTMVEDSCLSQPVTAFPQGTWIGEDIFPPLLPPT

EQDLTKLLLEGQGESGGGSLGAQPLLQPSHYGQSGISMSHMDLRANPSW" [SEQ ID No.9]
```
     polyA_signal    3924..3929
                     /gene="STAT6"
     polyA_site      3950
                     /gene="STAT6"
                     /evidence=experimental
     polyA_site      3969
                     /gene="STAT6"
                     /evidence=experimental
```

Figure 4 (continued)

polyA site   3978
             /gene="STAT6"
             /evidence=experimental
ORIGIN
        1 ccggaaacag cgggctgggg cagccactgc ttacactgaa gagggaggac gggagaggag
       61 tgtgtgtgtg tgtgtgtgtg tgtgtgtgta tgtatgtgtg tgctttatct tatttttctt
      121 tttggtggtg gtggtggaag ggggagggtg ctagcagggc cagccttgaa ctcgctggac
      181 agagctacag acctatgggg cctggaagtg cccgctgaga aagggagaag acagcagagg
      241 ggttgccgag gcaacctcca agtcccagat catgtctctg tggggtctgg tctccaagat
      301 gcccccagaa aaagtgcagc ggctctatgt cgactttccc caacacctgc ggcatcttct
      361 gggtgactgg ctggagagcc agccctggga gttcctggtc ggctccgacg ccttctgctg
      421 caacttggct agtgccctac tttcagacac tgtccagcac cttcaggcct cggtgggaga
      481 gcaggggggag gggagcacca tcttgcaaca catcagcacc cttgagagca tatatcagag
      541 ggacccctg aagctggtgg ccactttcag acaaatactt caaggagaga aaaaagctgt
      601 tatggaacag ttccgccact tgccaatgcc tttccactgg aagcaggaag aactcaagtt
      661 taagacaggc ttgcggaggc tgcagcaccg agtaggggag atccaccttc tccgagaagc
      721 cctgcagaag ggggctgagg ctggccaagt gtctctgcac agcttgatag aaactcctgc
      781 taatgggact gggccaagtg aggccctggc catgctactg caggagacca ctggagagct
      841 agaggcagcc aaagccctag tgctgaagag gatccagatt tggaaacggc agcagcagct
      901 ggcagggaat ggcgcaccgt ttgaggagag cctggcccca ctccaggaga ggtgtgaaag
      961 cctggtggac atttattccc agctacagca ggaggtaggg gcggctggtg gggagcttga
     1021 gcccaagacc cgggcatcgc tgactggccg gctggatgaa gtcctgagaa ccctcgtcac
     1081 cagttgcttc ctggtggaga agcagccccc caggtactg aagactcaga ccaagttcca
     1141 ggctggagtt cgattcctgt tgggcttgag gttcctgggg gccccagcca agcctccgct
     1201 ggtcagggcc gacatggtga cagagaagca ggcgcgggag ctgagtgtgc ctcagggtcc
     1261 tggggctgga gcagaaagca ctggagaaat catcaacaac actgtgccct ggagaacag
     1321 cattcctggg aactgctgct gccctgtt caagaacctg cttctcaaga agatcaagcg
     1381 gtgtgagcgg aagggcactg agtctgtcac agaggagaag tgcgctgtgc tcttctctgc
     1441 cagcttcaca cttggccccg gcaaactccc catccagctc caggccctgt ctctgccct
     1501 ggtggtcatc gtccatggca accaagacaa caatgccaaa gccactatcc tgtgggacaa
     1561 tgccttctct gagatggacc gcgtgccctt tgtggtggct gagcgggtgc cctgggagaa
     1621 gatgtgtgaa actctgaacc tgaagttcat ggctgaggtg gggaccaacc gggggctgct
     1681 cccagagcac ttcctcttcc tggcccagaa gatcttcaat gacaacagcc tcagtatgga
     1741 ggccttccag caccgttctg tgtcctggtc gcagttcaac aaggagatcc tgctgggccg
     1801 tggcttcacc ttttggcagt ggtttgatgg tgtcctggac ctcaccaaac gctgtctccg
     1861 gagctactgg tctgaccggc tgatcattgg cttcatcagc aaacagtacg ttactagcct
     1921 tcttctcaat gagcccgacg gaacctttct cctccgcttc agcgactcag agattgggggg
     1981 catcaccatt gcccatgtca tccgggggcca ggatggctct ccacagatag agaacatcca
     2041 gccattctct gccaaagacc tgtccattcg ctcactgggg gaccgaatcc gggatcttgc
     2101 tcagctcaaa aatctctatc caagaagcc caaggatgag gctttccgga gccactacaa
     2161 gcctgaacag atgggtaagg atgcaggggg ttatgtccca gctaccatca agatgaccgt
     2221 ggaaagggac caaccacttc ctaccccaga gctccagatg cctaccatgg tgccttctta
     2281 tgaccttgga atggccccctg attcctccat gagcatgcag cttggcccag atatggtgcc
     2341 ccaggtgtac ccaccacact ctcactccat ccccccgtat caaggcctct cccagaaga
     2401 atcagtcaac gtgttgtcag ccttccagga gcctcacctg cagatgcccc cagcctggg
     2461 ccagatgagc ctgcccttg accagcctca ccccagggc ctgctgccgt ccagcctca
     2521 ggagcatgct gtgtccagcc ctgaccccct gctctgctca gatgtgacca tggtggaaga
     2581 cagctgcctg agccagccag tgacagcgtt tcctcagggc acttggattg gtgaagacat
     2641 attccctcct ctgctgcctc ccactgaaca ggacctcact aagcttctcc tggagggca
     2701 aggggagtcg gggggagggt ccttgggggg cacagccctc ctgcagccct cccactatgg

```
2761 gcaatctggg atctcaatgt cccacatgga cctaagggcc aacccccagtt ggtgatccca
2821 gctggaggga gaacccaaag agacagctct tctactaccc ccacagacct gctctggaca
2881 cttgctcatg ccctgccaag cagcagatgg ggagggtgcc ctcctatccc cacctactcc
2941 tgggtcagga ggaaaagact aacaggagaa tgcacagtgg gtggagccaa tccactcctt
3001 cctttctatc attcccctgc ccacctcctt ccagcactga ctggaaggga agtcaggct
3061 ctgagacacg ccccaacatg cctgcacctg cagcgcgcac acgcacgcac acacacatac
3121 agagctctct gagggtgatg gggctgagca ggaggggggc tgggtaagag cacaggttag
3181 ggcatggaag gcttctccgc ccattctgac ccagggccta ggacggatag gcaggaacat
3241 acagacacat ttacactaga ggccagggat agaggatatt gggtctcagc cctaggggaa
3301 tgggaagcag ctcaagggac cctgggtggg agcataggag gggtctggac atgtggttac
3361 tagtacaggt tttgccctga ttaaaaaatc tcccaaagcc ccaaattcct gttagccagg
3421 tggaggcttc tgatacgtgt atgagactat gcaaaagtac aagggctgag attcttcgtg
3481 tatagctgtg tgaacgtgta tgtacctagg atatgttaaa tgtatagctg gcaccttagt
3541 tgcatgacca catagaacat gtgtctatct gcttttgcct acgtgacaac acaaatttgg
3601 gagggtgaga cactgcacag aagacagcag caagtgtgct ggcctctctg acatatgcta
3661 accccccaaat actctgaatt tggagtctga ctgtgcccaa gtgggtccaa gtggctgtga
3721 catctacgta tggctccaca cctccaatgc tgcctgggag ccagggtgag agtctgggtc
3781 caggcctggc catgtggccc tccagtgtat gagagggccc tgcctgctgc atcttctg
3841 ttgccccatc caccgccagc ttcccttcac tcccctatcc cattctccct ctcaaggcag
3901 gggtcataga tcctaagcca taaaataaat tttattccaa aataacaaaa taaataatct
3961 actgtacaca atctgaaaaa aaaaaaaaaa aaa           [SEQ ID No.10]
```

```
LOCUS       NM_009284            3213 bp    mRNA    linear   ROD 28-OCT-2004
DEFINITION  Mus musculus signal transducer and activator of transcription 6
            (Stat6), mRNA.
ACCESSION   NM_009284
VERSION     NM_009284.1  GI:6678154
KEYWORDS
SOURCE      Mus musculus (house mouse)
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus.
COMMENT     PROVISIONAL REFSEQ: This record has not yet been subject to final
            NCBI review. The reference sequence was derived from L47650.1.
FEATURES             Location/Qualifiers
     source          1..3213
                     /organism="Mus musculus"
                     /mol_type="mRNA"
                     /db_xref="taxon:10090"
                     /chromosome="10"
                     /map="10 70.0 cM"
     gene            1..3213
                     /gene="Stat6"
                     /db_xref="GeneID:20852"
                     /db_xref="MGI:103034"
     CDS             280..2793
                     /gene="Stat6"
                     /function="DNA-Binding Protein and transcription factor"
                     /note="go_component: nucleus [goid 0005634] [evidence IDA]
                     [pmid 12093868];
                     go_component: cytoplasm [goid 0005737] [evidence IDA]
                     [pmid 12093868];
                     go_component: cytoplasm [goid 0005737] [evidence IDA]
                     [pmid 12634107];
                     go_function: DNA binding [goid 0003677] [evidence IEA];
                     go_function: signal transducer activity [goid 0004871]
                     [evidence IEA];
                     go_function: transcription factor activity [goid 0003700]
                     [evidence IEA];
                     go_process: signal transduction [goid 0007165] [evidence
                     IEA];
                     go_process: intracellular signaling cascade [goid 0007242]
                     [evidence IEA];
                     go_process: regulation of cell proliferation [goid
                     0042127] [evidence IDA] [pmid 12093868];
                     go_process: regulation of transcription, DNA-dependent
                     [goid 0006355] [evidence IEA]"
                     /codon_start=1
                     /product="signal transducer and activator of transcription
```

Figure 5

6"
/protein_id="NP_033310.1"
/db_xref="GI:6678155"
/db_xref="GeneID:20852"
/db_xref="MGI:103034"

/translation="MSLWGLISKMSPEKLQRLYVDFPQRLRHLLADWLESQPWEFLVG

SDAFCYNMASALLSATVQRLQATAGEQGKGNSILPHISTLESIYQRDPLKLVATIRQI

LQGEKKAVIEEFRHLPGPFHRKQEELKFTTPLGRLHHRVRETRLLRESLHLGPKTGQV

SLQNLIDPPLNGPGPSEDLPTILQGTVGDLETTQPLVLLRIQIWKRQQQLAGNGTPFE

ESLAGLQERCESLVEIYSQLHQEIGAASGELEPKTRASLISRLDEVLRTLVTSSFLVE

KQPPQVLKTQTKFQAGVRFLLGLQFLGTSTKPPMVRADMVTEKQARELSLSQGPGTGV

ESTGEIMNNTVPLENSIPSNCCSALFKNLLLKKIKRCERKGTESVTEEKCAVLFSTSF

TLGPNKLLIQLQALSLSLVVIVHGNQDNNAKATILWDNAFSEMDRVPFVVGERVPWEK

MCETLNLKFMVEVGTSRGLLPEHFLFLAQKIFNDNSLSVEAFQHRCVSWSQFNKEILL

GRGFTFWQWFDGVLDLTKRCLRSYWSDRLIIGFISKQYVTSLLLNEPDGTFLLRFSDS

EIGGITIAHVIRGQDGSSQIENIQPFSAKDLSIRSLGDRIRDLAQLKNLYPKKPKDEA

FRSHYKPEQMGKDGRGYVSTTIKMTVERDQPLPTPEPQMPAMVPPYDLGMAPDASMQL

SSDMGYPPQSIHSFQSLEESMSVLPSFQEPHLQMPPNMSQITMPFDQPHPQGLLQCQS

QEHAVSSPEPMLWSDVTMVEDSCLTQPVGGFPQGTWVSEDMYPPLLPPTEQDLTKLLL

ENQGEGGGSLGSQPLLKPSPYGQSGISLSHLDLRTNPSW"      [SEQ ID No.11]

ORIGIN
    1 gccgctctaa cgcaacacgc cctctgtcgg caggtaattg cactgcccgg tctcacctaa
   61 ctatgcacgt aaacaatcct cactcggac gaactgggtt gtgcacgctg gacctgggca
  121 agaggaaacc accccaggcc caggtccggg ctcaagcccg cccgattgtc agaagagaac
  181 cgctggacag acctacagac ccatggggct tggtagtgcc ctctgagaga gggagaagat
  241 agcagcgggg ctgccgaggc accctgtata tccagatca tgtctctgtg gggcctaatt
  301 tccaagatgt ccccagaaaa actgcaacgg ctctatgttg actttccaca acgcctacgg
  361 catctcctgg ctgactggct ggagagccag ccctgggagt tcctggtcgg ttcagatgct
  421 ttctgttaca acatggccag tgccctactt tctgccaccg tccagcgtct tcaggccact
  481 gctggagagc aggggaaggg aaacagcatc ttgccgcaca tcagcacctt ggagagcatc
  541 tatcagaggg accccctgaa gctggtggcc accatcagac aaatacttca aggggagaaa
  601 aaagctgtta tagaagagtt ccgccacctg ccagggccct tccatcggaa gcaggaagaa
  661 ctcaagttta ctacacccct cggaaggctt caccatcgag taagggagac ccggcttctc

```
 721 cgagaatctc tacacctagg gcctaagact ggacaagtgt ctctgcagaa tttgatagac
 781 cctcctctca atggtcctgg tccaagtgag gacctgccca ccatactcca ggggactgtg
 841 ggggacctgg agaccaccca gcccctggtt ctgttaagga ttcagatttg gaagcggcag
 901 caacagctgg cagggaatgg cacacccttt gaggagagcc tagcagggct ccaggagagg
 961 tgtgaaagcc tggtggaaat ttattcccag ctccaccagg agattggggc agccagtggg
1021 gaactggaac ccaagacccg ggcatcgctg ataagccgtc tggatgaagt cctgcgaacc
1081 cttgtgacca gctctttcct ggtggagaag cagcccccc aggttctgaa gacacagact
1141 aagttccagg ctggggttcg attcctgctg ggtctgcagt ttctagggac ctcaaccaag
1201 cctccaatgg tcagagctga catggtgaca gagaaacagg ccagagaact aagtctgtcc
1261 caggggcccg ggactggagt ggagagcaca ggagagatca tgaacaacac ggtgccctg
1321 gagaacagca ttcccagcaa ctgctgctcc gccctgttca agaacctgct cctgaagaaa
1381 ataaagcgct gtgagcggaa gggcacagag tctgtcaccg aggagaagtg tgctgtgctc
1441 ttctccacga gcttcacatt gggccccaac aaacttctca tccagcttca ggccctgtct
1501 ctgtccttgg tggtcatcgt gcatggtaac caagacaaca cgccaaagc taccatccta
1561 tgggacaatg ccttctctga gatggaccga gtgcccttg tggtgggtga gcgagtgccc
1621 tgggagaaga tgtgtgaaac cctaaacctc aagtttatgg ttgaggtggg gaccagccgg
1681 ggactgcttc cagagcactt cctgttcctc gcccagaaga tcttcaacga caacagcctc
1741 agtgtggagg cctttcagca ccgctgtgtg tcctggtcac agttcaataa ggagatcctg
1801 ctgggccgag gcttcacatt ttggcagtgg tttgatggtg tcctggacct caccaaacgc
1861 tgtctccgga gctactggtc agatcggctg atcattggct ttattagtaa gcaatatgtc
1921 actagccttc tcctcaatga gccagatggg accttcctcc tccgctttag cgactctgag
1981 atcgggggca tcaccattgc acacgtcatc cggggtcagg atggctcctc acagatagag
2041 aacatccagc cattttctgc caaagacctg tccattcgct cactggggga ccggatccgg
2101 gatcttgctc agttaaaaaa cctctacccc aagaaaccca agatgaggc tttccggagt
2161 cactataagc ccgaacagat ggggaaggac gggagggggtt atgtctctac tactatcaag
2221 atgactgtgg aaagggacca gcccttcct actccagagc cccagatgcc tgccatggtg
2281 ccaccttatg atcttggaat ggccctgat gcttccatgc aactcagctc agatatgggg
2341 tatcctccac agtccatcca ctcatttcag agcctagaag agtccatgag tgtactgcca
2401 tcttttcagg agcctcacct gcaaatgccc cccaacatga gccagataac catgcccttt
2461 gaccagcctc accccaggg tctgctgcag tgccagtccc aggaacatgc tgtgtccagc
2521 cctgaaccca tgctttggtc agatgtgact atggtagagg acagttgcct aactcagcct
2581 gtgggaggtt tccccaagg cacctgggtc agtgaagaca tgtaccctcc cctgctgcct
2641 cccactgaac aggacctcac caagcttctc ctggagaacc aaggggaggg aggagggtcc
2701 ttaggaagcc agccctcct gaaaccatct ccttatgggc aatcagggat ctcactgtcc
2761 cacctggacc taaggaccaa ccccagctgg tgatcccagc tggagaagcc cagaaacaaa
2821 gcctcttctg tctctatgga ccagctctgg cacctgctc atgcaggtgc cttccgtctc
2881 aactgttcct tggttaagag aaaagaactg gctgggagac catgtggtgt atggaactgc
2941 tgtgctctgt cctacctgcc atatcagggc ccccttttc cagcactggg tgcaaaggga
3001 tgagtgggt gttaatgctc gaatgtgata caactgtatc acaacacaca cgcacacaca
3061 tacacacaca ccagaactgt gttgagccag ggcctggac tcaacataca gaaacataga
3121 gacattgtgc ccaagacag aggacatata gccctagggc attgaagctg ggctcagtga
3181 ctctgggagg gagaaaaagg aaaaagtggg tat         [SEQ ID No.12]
```

```
LOCUS       XM_343223               2442 bp    mRNA    linear   ROD 24-OCT-2003
DEFINITION  Rattus norvegicus similar to signal transducer and activator of
            transcription 6 (LOC362896), mRNA.
ACCESSION   XM_343223
VERSION     XM_343223.1  GI:34865760
KEYWORDS
SOURCE      Rattus norvegicus (Norway rat)
  ORGANISM  Rattus norvegicus
            Eukaryota; Metazoa; Chordata; Craniata; Vertebrata; Euteleostomi;
            Mammalia; Eutheria; Rodentia; Sciurognathi; Muridae; Murinae;
            Rattus.
COMMENT     MODEL REFSEQ: This record is predicted by automated computational
            analysis. This record is derived from an annotated genomic sequence
            (NW_047777) using gene prediction method: GNOMON, supported by EST
            evidence.
            Also see:
                Documentation of NCBI's Annotation Process FEATURES             Location/Qualifiers
     source          1..2442
                     /organism="Rattus norvegicus"
                     /mol_type="mRNA"
                     /strain="BN/SsNHsdMCW"
                     /db_xref="taxon:10116"
                     /chromosome="7"
     gene            1..2442
                     /gene="LOC362896"
                     /note="Derived by automated computational analysis using
                     gene prediction method: GNOMON."
                     /db_xref="InterimID:362896"
     CDS             1..2442
                     /gene="LOC362896"
                     /codon_start=1
                     /product="similar to signal transducer and activator of
                     transcription 6"
                     /protein_id="XP_343224.1"
                     /db_xref="GI:34865761"
                     /db_xref="InterimID:362896"
```

/translation="MSLWSLVSKMSPEKLQRLYVDFPQHLRHLLAEWLENQPWEFLVG

SDAFCYNMASALLSATVQRLQASAGEQGKGSSLLQHISTLESIYQRDPLKLVATIRQI

LQGEKKAVIEEFHHLPGPFHRKQEELKFTTALGRLQHRVRETRILRESLQQGTKTAQV

SLKNLIDPPANGTGPSEDLATMLQGTVGDLEATQALVLKRIQIWKRQQQLAGNGTPFE

Figure 6

ESLAGLQERCESLVEIYSQLQQEIGAASGELEPKTRASLISRLDEVLRTLVTSSFLVE

KQPPQVLKTQTKFQAGVRFLLGLQFLGTSAKPPLVRADMVTEKQARELSLPQGSGAGV

ESTGEIMNNTVPLENSVPGNCCSALFKNLLLKKIKRCERKGTESVTEEKCAVLFSTSF

MLGPNKHLIQLQALSLPLVVIVHGNQDNNAKATILWDNAFSEMDRVPFVVAERVPWEK

MCETLNLKFMAEVGTSRGLLPEHFLFLAQKIFNDNSLSIEAFQHRCVSWSQFNKEILL

GRGFTFWQWFDGVLDLTKRCLRSYWSDRLIIGFISKQYVTSLLLNEPDGTFLLRFSDS

EIGGITIAHVIRGQDGSSQIENIQPFSAKDLSIRSLGDRIRDLAQLKNLYPKKPKDEA

FRSHYKPEQMGKDGRGYVSTTIKMTVERDQPLPTPEPQMPAMVAPYDLGMAPDASMQL

SSDMVPHLQMPPTMSQISMPFDQPHPQGLLQCQSQEHAVSSPEPLLCSDVTMAEDSCL

TQPVQGFPQGTWVSEGMYPPLMPPTEQDLTKLLLEGQGEGGGSIGTQPLLQPSSYGQS

GISMSHLDLRTNPSW"        [SEQ ID No.13]
    misc feature    4..348
            /gene="LOC362896"
            /note="STAT_prot; Region: STAT protein, protein
            interaction domain. STAT proteins (Signal Transducers and
            Activators of Transcription) are a family of transcription
            factors that are specifically activated to regulate gene
            transcription when cells encounter cytokines and growth
            factors. STAT proteins also include an SH2 domain
            pfam00017"
            /db_xref="CDD:pfam02865"
    misc feature    370..813
            /gene="LOC362896"
            /note="STAT; Region: STAT protein, all-alpha domain. STAT
            proteins (Signal Transducers and Activators of
            Transcription) are a family of transcription factors that
            are specifically activated to regulate gene transcription
            when cells encounter cytokines and growth factors. STAT
            proteins also include an SH2 domain pfam00017"
            /db_xref="CDD:pfam01017"
    misc feature    817..1581
            /gene="LOC362896"
            /note="STAT_bind; Region: STAT protein, DNA binding
            domain. STAT proteins (Signal Transducers and Activators
            of Transcription) are a family of transcription factors
            that are specifically activated to regulate gene
            transcription when cells encounter cytokines and growth
            factors. This family represents the DNA binding domain of
            STAT, which has an ig-like fold. STAT proteins also

Figure 6 (continued)

```
                include an SH2 domain pfam00017"
                /db_xref="CDD:pfam02864"
     misc_feature    1612..1848
                /gene="LOC362896"
                /note="SH2; Region: SH2 domain"
                /db_xref="CDD:pfam00017"
     misc_feature    1618..1860
                /gene="LOC362896"
                /note="SH2; Region: Src homology 2 domains"
                /db_xref="CDD:smart00252"
ORIGIN
        1 atgtctctgt ggagtctagt ttccaagatg tccccagaaa aactgcaacg gctctatgtt
       61 gactttccac aacacctgcg gcatcttctg gccgaatggc tggagaatca gccctgggag
      121 ttcctggttg gttcagatgc tttctgttac aacatggcta gtgccctact ttctgccact
      181 gtccagcgtc ttcaggcctc tgcaggagag caggggaaag gaagcagcct cttgcagcac
      241 atcagcacct tggagagcat ctatcagagg gacccctga agctggtggc caccatcaga
      301 caaatacttc aaggggagaa aaagctgtt ataagaagt tccaccacct gccagggccc
      361 ttccatcgaa agcaggaaga actcaagttt actacagccc tgggcaggct tcagcaccga
      421 gtaagggaga ccaggattct ccgagaatct ctgcagcagg gaccaagac tgcgcaagtg
      481 tctctgaaga acttgataga ccctcctgcc aatggcactg gtccaagtga ggatctggcc
      541 acgatgctgc aggggactgt gggggacttg gaggccaccc aggctctagt gctgaaaagg
      601 attcagattt ggaagcggca acagcagctg gcaggaatg gcacacccct tgaggagagc
      661 ctggcagggc tgcaggagag gtgtgaaagc ctggtggaaa tttattccca gctgcagcag
      721 gagattggag cagccagtgg ggagcttgag cccaagaccc gggcatcgct cataagccgt
      781 ctggatgaag tcctgcgaac cctcgtgacc agctctttcc tggtggagaa gcagccccca
      841 caggttctga agacacagac taagtttcag gctgggtc gattcctact gggtctgcag
      901 ttcctaggga cctcagccaa gcctccactg gtcagagctg acatggtgac agagaaacag
      961 gccagagaac taagcctgcc ccagggtct ggggctggag tggagagcac aggagagatc
     1021 atgaacaata ctgtacctc ggagaacagt gttcctggga actgctgctc tgcctcttc
     1081 aagaacctgc tcctgaagaa aatcaagcgc tgtgagcgga agggtacaga gtctgtcacc
     1141 gaagagaagt gcgctgtgct cttctctacg agcttcatgc tgggccccaa caaacacctc
     1201 atccagcttc aggccctgtc tctgcccttg gtggtcatcg ttcatggcaa ccaagacaac
     1261 aatgccaaag ctaccatcct gtgggataat gccttctctg agatggaccg agtgccctt
     1321 gtggtagctg agcgagtgcc ctgggagaaa atgtgtgaaa ctctgaacct caagtttatg
     1381 gctgaggtgg ggaccagccg gggactgcta ccagaacact tcctgttcct ggcccagaag
     1441 atcttcaatg acaacagcct agcatagag gcctttcagc accgctgtgt gtcttggtca
     1501 cagttcaaca aggagattct actgggccga ggcttcactt tttggcagtg gtttgatggt
     1561 gtcctggacc tcactaaacg ctgtcttcgg agctactggt cagatcggct gatcatcggc
     1621 tttatcagta agcaatatgt cactagcctt ctcctcaacg agccagatgg aaccttcctc
     1681 ctccgcttta gcgactctga gattgggggc atcaccattg cccatgtcat ccgggtcag
     1741 gatggctcct cacagataga gaacatccag ccgttttctg ccaaagacct atccatcgc
     1801 tcactgggggg accgaatccg agatcttgct caattaaaaa acctctaccc caagaaaccc
     1861 aaggatgagg cttttcggag ccactataag ccggaacaga tgggaaagga cgggagggggt
     1921 tatgtctcaa ctactatcaa gatgactgtg gaaagggacc agcccccttcc tactccagag
     1981 ccccagatgc ctgccatggt ggccccttat gatcttggaa tggccctga tgcttccatg
     2041 caactcagct cagatatggt gcctcacctt caaatgcccc caccatgag ccagataagc
     2101 atgccctttg accagcctca tccccagggc ctgctccagt gccagtccca ggagcatgcg
     2161 gtgtccagcc ctgaacccct gctgtgttca gatgtcacta tggcggaaga cagctgccta
     2221 actcagcctg tgcaaggttt cccccagggc acctgggtca gcgaaggcat gtaccctccc
     2281 ctgatgcctc ccactgaaca ggacctcacc aagcttctcc tagagggcca aggggaaggt
```

Figure 6 (continued)

2341 ggaggatcca tagggactca gcccctcctg caaccatctt cttatgggca atcggggatc
2401 tcaatgtccc acctggacct aaggaccaac cccagttggt ga        [SEQ ID No.14]

Figure 6 (continued)

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial sequence
<220> FEATURE:
<223> OTHER INFORMATION: siRNA

<400> SEQUENCE: 1
gcaggaagaa cucaaguuut t                                                  21

<210> SEQ ID NO 2
<211> LENGTH: 21
<212> TYPE: DNA
<213> ORGANISM: Artificial sequence
<220> FEATURE:
<223> OTHER INFORMATION: siRNA

<400> SEQUENCE: 2
acaguacguu acuagccuut t                                                  21

<210> SEQ ID NO 3
<211> LENGTH: 21
<212> TYPE: DNA
<213> ORGANISM: Artificial sequence
<220> FEATURE:
<223> OTHER INFORMATION: siRNA

<400> SEQUENCE: 3
```

```
gaaucaguca acguguugut t                                              21

<210> SEQ ID NO 4
<211> LENGTH: 21
<212> TYPE: DNA
<213> ORGANISM: Artificial sequence
<220> FEATURE:
<223> OTHER INFORMATION: siRNA

<400> SEQUENCE: 4
agcacuggag aaaucaucat t                                              21

<210> SEQ ID NO 5
<211> LENGTH: 19
<212> TYPE: DNA
<213> ORGANISM: Homo sapiens

<400> SEQUENCE: 5
gcaggaagaa cucaaguuu                                                 19

<210> SEQ ID NO 6
<211> LENGTH: 19
<212> TYPE: DNA
<213> ORGANISM: Homo sapiens

<400> SEQUENCE: 6
acaguacguu acuagccuu                                                 19

<210> SEQ ID NO 7
<211> LENGTH: 19
<212> TYPE: DNA
<213> ORGANISM: Homo sapiens

<400> SEQUENCE: 7
gaaucaguca acguguugu                                                 19

<210> SEQ ID NO 8
<211> LENGTH: 19
<212> TYPE: DNA
<213> ORGANISM: Homo sapiens

<400> SEQUENCE: 8
agcacuggag aaaucauca                                                 19

<210> SEQ ID NO 9
<211> LENGTH: 847
<212> TYPE: PRT
<213> ORGANISM: Homo sapiens

<400> SEQUENCE: 9
```

| Met | Ser | Leu | Trp | Gly | Leu | Val | Ser | Lys | Met | Pro | Pro | Glu | Lys | Val | Gln |
|---|---|---|---|---|---|---|---|---|---|---|---|---|---|---|---|
| 1 |  |  |  | 5 |  |  |  |  | 10 |  |  |  |  | 15 |  |

| Arg | Leu | Tyr | Val | Asp | Phe | Pro | Gln | His | Leu | Arg | His | Leu | Leu | Gly | Asp |
|---|---|---|---|---|---|---|---|---|---|---|---|---|---|---|---|
|  |  |  | 20 |  |  |  |  | 25 |  |  |  |  | 30 |  |  |

| Trp | Leu | Glu | Ser | Gln | Pro | Trp | Glu | Phe | Leu | Val | Gly | Ser | Asp | Ala | Phe |
|---|---|---|---|---|---|---|---|---|---|---|---|---|---|---|---|
|  |  | 35 |  |  |  |  | 40 |  |  |  |  | 45 |  |  |  |

| Cys | Cys | Asn | Leu | Ala | Ser | Ala | Leu | Leu | Ser | Asp | Thr | Val | Gln | His | Leu |
|---|---|---|---|---|---|---|---|---|---|---|---|---|---|---|---|
|  | 50 |  |  |  |  | 55 |  |  |  |  | 60 |  |  |  |  |

| Gln | Ala | Ser | Val | Gly | Glu | Gln | Gly | Glu | Gly | Ser | Thr | Ile | Leu | Gln | His |
|---|---|---|---|---|---|---|---|---|---|---|---|---|---|---|---|
| 65 |  |  |  |  | 70 |  |  |  |  | 75 |  |  |  |  | 80 |

| Ile | Ser | Thr | Leu | Glu | Ser | Ile | Tyr | Gln | Arg | Asp | Pro | Leu | Lys | Leu | Val |

-continued

```
                85                  90                  95
Ala Thr Phe Arg Gln Ile Leu Gln Gly Glu Lys Lys Ala Val Met Glu
            100                 105                 110
Gln Phe Arg His Leu Pro Met Pro Phe His Trp Lys Gln Glu Glu Leu
            115                 120                 125
Lys Phe Lys Thr Gly Leu Arg Arg Leu Gln His Arg Val Gly Glu Ile
            130                 135                 140
His Leu Leu Arg Glu Ala Leu Gln Lys Gly Ala Glu Ala Gly Gln Val
145                 150                 155                 160
Ser Leu His Ser Leu Ile Glu Thr Pro Ala Asn Gly Thr Gly Pro Ser
            165                 170                 175
Glu Ala Leu Ala Met Leu Leu Gln Glu Thr Thr Gly Glu Leu Glu Ala
            180                 185                 190
Ala Lys Ala Leu Val Leu Lys Arg Ile Gln Ile Trp Lys Arg Gln Gln
            195                 200                 205
Gln Leu Ala Gly Asn Gly Ala Pro Phe Glu Glu Ser Leu Ala Pro Leu
            210                 215                 220
Gln Glu Arg Cys Glu Ser Leu Val Asp Ile Tyr Ser Gln Leu Gln Gln
225                 230                 235                 240
Glu Val Gly Ala Ala Gly Gly Glu Leu Glu Pro Lys Thr Arg Ala Ser
            245                 250                 255
Leu Thr Gly Arg Leu Asp Glu Val Leu Arg Thr Leu Val Thr Ser Cys
            260                 265                 270
Phe Leu Val Glu Lys Gln Pro Pro Gln Val Leu Lys Thr Gln Thr Lys
            275                 280                 285
Phe Gln Ala Gly Val Arg Phe Leu Leu Gly Leu Arg Phe Leu Gly Ala
            290                 295                 300
Pro Ala Lys Pro Pro Leu Val Arg Ala Asp Met Val Thr Glu Lys Gln
305                 310                 315                 320
Ala Arg Glu Leu Ser Val Pro Gln Gly Pro Gly Ala Gly Ala Glu Ser
            325                 330                 335
Thr Gly Glu Ile Ile Asn Asn Thr Val Pro Leu Glu Asn Ser Ile Pro
            340                 345                 350
Gly Asn Cys Cys Ser Ala Leu Phe Lys Asn Leu Leu Leu Lys Lys Ile
            355                 360                 365
Lys Arg Cys Glu Arg Lys Gly Thr Glu Ser Val Thr Glu Glu Lys Cys
            370                 375                 380
Ala Val Leu Phe Ser Ala Ser Phe Thr Leu Gly Pro Gly Lys Leu Pro
385                 390                 395                 400
Ile Gln Leu Gln Ala Leu Ser Leu Pro Leu Val Val Ile Val His Gly
            405                 410                 415
Asn Gln Asp Asn Asn Ala Lys Ala Thr Ile Leu Trp Asp Asn Ala Phe
            420                 425                 430
Ser Glu Met Asp Arg Val Pro Phe Val Val Ala Glu Arg Val Pro Trp
            435                 440                 445
Glu Lys Met Cys Glu Thr Leu Asn Leu Lys Phe Met Ala Glu Val Gly
            450                 455                 460
Thr Asn Arg Gly Leu Leu Pro Glu His Phe Leu Phe Leu Ala Gln Lys
465                 470                 475                 480
Ile Phe Asn Asp Asn Ser Leu Ser Met Glu Ala Phe Gln His Arg Ser
            485                 490                 495
Val Ser Trp Ser Gln Phe Asn Lys Glu Ile Leu Leu Gly Arg Gly Phe
            500                 505                 510
```

```
Thr Phe Trp Gln Trp Phe Asp Gly Val Leu Asp Leu Thr Lys Arg Cys
            515                 520                 525
Leu Arg Ser Tyr Trp Ser Asp Arg Leu Ile Ile Gly Phe Ile Ser Lys
            530                 535                 540
Gln Tyr Val Thr Ser Leu Leu Asn Glu Pro Asp Gly Thr Phe Leu
545                 550                 555                 560
Leu Arg Phe Ser Asp Ser Glu Ile Gly Gly Ile Thr Ile Ala His Val
            565                 570                 575
Ile Arg Gly Gln Asp Gly Ser Pro Gln Ile Glu Asn Ile Gln Pro Phe
            580                 585                 590
Ser Ala Lys Asp Leu Ser Ile Arg Ser Leu Gly Asp Arg Ile Arg Asp
            595                 600                 605
Leu Ala Gln Leu Lys Asn Leu Tyr Pro Lys Lys Pro Lys Asp Glu Ala
            610                 615                 620
Phe Arg Ser His Tyr Lys Pro Glu Gln Met Gly Lys Asp Gly Arg Gly
625                 630                 635                 640
Tyr Val Pro Ala Thr Ile Lys Met Thr Val Glu Arg Asp Gln Pro Leu
            645                 650                 655
Pro Thr Pro Glu Leu Gln Met Pro Thr Met Val Pro Ser Tyr Asp Leu
            660                 665                 670
Gly Met Ala Pro Asp Ser Ser Met Ser Met Gln Leu Gly Pro Asp Met
            675                 680                 685
Val Pro Gln Val Tyr Pro Pro His Ser His Ser Ile Pro Pro Tyr Gln
            690                 695                 700
Gly Leu Ser Pro Glu Glu Ser Val Asn Val Leu Ser Ala Phe Gln Glu
705                 710                 715                 720
Pro His Leu Gln Met Pro Pro Ser Leu Gly Gln Met Ser Leu Pro Phe
            725                 730                 735
Asp Gln Pro His Pro Gln Gly Leu Leu Pro Cys Gln Pro Gln Glu His
            740                 745                 750
Ala Val Ser Ser Pro Asp Pro Leu Leu Cys Ser Asp Val Thr Met Val
            755                 760                 765
Glu Asp Ser Cys Leu Ser Gln Pro Val Thr Ala Phe Pro Gln Gly Thr
770                 775                 780
Trp Ile Gly Glu Asp Ile Phe Pro Pro Leu Leu Pro Pro Thr Glu Gln
785                 790                 795                 800
Asp Leu Thr Lys Leu Leu Leu Glu Gly Gln Gly Glu Ser Gly Gly Gly
            805                 810                 815
Ser Leu Gly Ala Gln Pro Leu Leu Gln Pro Ser His Tyr Gly Gln Ser
            820                 825                 830
Gly Ile Ser Met Ser His Met Asp Leu Arg Ala Asn Pro Ser Trp
            835                 840                 845

<210> SEQ ID NO 10
<211> LENGTH: 3993
<212> TYPE: DNA
<213> ORGANISM: Homo sapiens

<400> SEQUENCE: 10
ccggaaacag cgggctgggg cagccactgc ttacactgaa gagggaggac gggagaggag      60
tgtgtgtgtg tgtgtgtgtg tgtgtgtgta tgtatgtgtg tgctttatct tatttttctt     120
tttggtggtg gtggtggaag gggggaggtg ctagcagggc cagccttgaa ctcgctggac     180
agagctacag acctatgggg cctggaagtg cccgctgaga aagggagaag acagcagagg     240
```

-continued

| | |
|---|---|
| ggttgccgag gcaacctcca agtcccagat catgtctctg tggggtctgg tctccaagat | 300 |
| gcccccagaa aaagtgcagc ggctctatgt cgactttccc caacacctgc ggcatcttct | 360 |
| gggtgactgg ctggagagcc agccctggga gttcctggtc ggctccgacg ccttctgctg | 420 |
| caacttggct agtgccctac tttcagacac tgtccagcac cttcaggcct cggtgggaga | 480 |
| gcaggggag gggagcacca tcttgcaaca catcagcacc cttgagagca tatatcagag | 540 |
| ggaccccctg aagctggtgg ccactttcag acaaatactt caaggagaga aaaagctgt | 600 |
| tatggaacag ttccgccact tgccaatgcc tttccactgg aagcaggaag aactcaagtt | 660 |
| taagacaggc ttgcggaggc tgcagcaccg agtagggag atccaccttc tccgagaagc | 720 |
| cctgcagaag ggggctgagg ctggccaagt gtctctgcac agcttgatag aaactcctgc | 780 |
| taatgggact gggccaagtg aggccctggc catgctactg caggagacca ctggagagct | 840 |
| agaggcagcc aaagccctag tgctgaagag gatccagatt tggaaacggc agcagcagct | 900 |
| ggcagggaat ggcgcaccgt tgaggagag cctggcccca ctccaggaga ggtgtgaaag | 960 |
| cctggtggac atttattccc agctacagca ggaggtaggg gcggctggtg gggagcttga | 1020 |
| gcccaagacc cgggcatcgc tgactggccg gctggatgaa gtcctgagaa ccctcgtcac | 1080 |
| cagttgcttc ctggtggaga agcagccccc ccaggtactg aagactcaga ccaagttcca | 1140 |
| ggctggagtt cgattcctgt tgggcttgag gttcctgggg ccccagcca agcctccgct | 1200 |
| ggtcagggcc gacatggtga cagagaagca ggcgcgggag ctgagtgtgc ctcagggtcc | 1260 |
| tggggctgga gcagaaagca ctggagaaat catcaacaac actgtgccct tggagaacag | 1320 |
| cattcctggg aactgctgct ctgccctgtt caagaacctg cttctcaaga agatcaagcg | 1380 |
| gtgtgagcgg aagggcactg agtctgtcac agaggagaag tgcgctgtgc tcttctctgc | 1440 |
| cagcttcaca cttggccccg gcaaactccc catccagctc caggccctgt ctctgcccct | 1500 |
| ggtggtcatc gtccatggca accaagacaa caatgccaaa gccactatcc tgtgggacaa | 1560 |
| tgccttctct gagatggacc gcgtgccctt tgtggtggct gagcgggtgc cctgggagaa | 1620 |
| gatgtgtgaa actctgaacc tgaagttcat ggctgaggtg gggaccaacc gggggctgct | 1680 |
| cccagagcac ttcctcttcc tggcccagaa gatcttcaat gacaacagcc tcagtatgga | 1740 |
| ggccttccag caccgttctg tgtcctggtc gcagttcaac aaggagatcc tgctgggccg | 1800 |
| tggcttcacc ttttggcagt ggtttgatgg tgtcctggac ctcaccaaac gctgtctccg | 1860 |
| gagctactgt tctgaccggc tgatcattgg cttcatcagc aaacagtacg ttactagcct | 1920 |
| tcttctcaat gagcccgacg gaacctttct cctccgcttc agcgactcag agattggggg | 1980 |
| catcaccatt gccatgtca tccggggcca ggatggctct ccacagatag agaacatcca | 2040 |
| gccattctct gccaaagacc tgtccattcg ctcactgggg gaccgaatcc gggatcttgc | 2100 |
| tcagctcaaa aatctctatc caagaagcc caaggatgag gctttccgga gccactacaa | 2160 |
| gcctgaacag atgggtaagg atggcagggg ttatgtccca gctaccatca gatgaccgt | 2220 |
| ggaaagggac caaccacttc ctaccccaga gctccagatg cctaccatgg tgccttctta | 2280 |
| tgaccttgga atggcccctg attcctccat gagcatgcag cttggcccag atatggtgcc | 2340 |
| ccaggtgtac ccaccacact ctcactccat cccccgtat caaggcctct ccccagaaga | 2400 |
| atcagtcaac gtgttgtcag ccttccagga gcctcacctg cagatgcccc ccagcctggg | 2460 |
| ccagatgagc ctgcccttttg accagcctca ccccagggc ctgctgccgt gccagcctca | 2520 |
| ggagcatgct gtgtccagcc ctgaccccct gctctgctca gatgtgacca tggtggaaga | 2580 |

```
cagctgcctg agccagccag tgacagcgtt tcctcagggc acttggattg gtgaagacat    2640
attccctcct ctgctgcctc ccactgaaca ggacctcact aagcttctcc tggaggggca    2700
aggggagtcg gggggagggt ccttgggggc acagcccctc ctgcagccct cccactatgg    2760
gcaatctggg atctcaatgt cccacatgga cctaagggcc aaccccagtt ggtgatccca    2820
gctggaggga gaacccaaag agacagctct tctactaccc ccacagacct gctctggaca    2880
cttgctcatg ccctgccaag cagcagatgg ggagggtgcc ctcctatccc cacctactcc    2940
tgggtcagga ggaaaagact aacaggagaa tgcacagtgg gtggagccaa tccactcctt    3000
cctttctatc attcccctgc ccacctcctt ccagcactga ctggaaggga agttcaggct    3060
ctgagacacg ccccaacatg cctgcacctg cagcgcgcac acgcacgcac acacacatac    3120
agagctctct gagggtgatg gggctgagca ggagggggggc tgggtaagag cacaggttag    3180
ggcatggaag gcttctccgc ccattctgac ccagggccta ggacggatag caggaacat    3240
acagacacat ttacactaga ggccagggat agaggatatt gggtctcagc cctaggggaa    3300
tgggaagcag ctcaagggac cctgggtggg agcataggag gggtctggac atgtggttac    3360
tagtacaggt tttgccctga ttaaaaaatc tcccaaagcc ccaaattcct gttagccagg    3420
tggaggcttc tgatacgtgt atgagactat gcaaaagtac aagggctgag attcttcgtg    3480
tatagctgtg tgaacgtgta tgtacctagg atatgttaaa tgtatagctg caccttagt    3540
tgcatgacca catagaacat gtgtctatct gcttttgcct acgtgacaac acaaatttgg    3600
gagggtgaga cactgcacag aagacagcag caagtgtgct ggcctctctg acatatgcta    3660
accccccaaat actctgaatt tggagtctga ctgtgcccaa gtgggtccaa gtggctgtga    3720
catctacgta tggctccaca cctccaatgc tgcctgggag ccagggtgag agtctgggtc    3780
caggcctggc catgtggccc tccagtgtat gagagggccc tgcctgctgc atctttctg    3840
ttgccccatc caccgccagc ttcccttcac tcccctatcc cattctccct ctcaaggcag    3900
gggtcataga tcctaagcca taaataaat tttattccaa aataacaaaa taaataatct    3960
actgtacaca atctgaaaaa aaaaaaaaaa aaa                                 3993
```

<210> SEQ ID NO 11
<211> LENGTH: 837
<212> TYPE: PRT
<213> ORGANISM: Mus musculus

<400> SEQUENCE: 11

```
Met Ser Leu Trp Gly Leu Ile Ser Lys Met Ser Glu Lys Leu Gln
1               5                   10                  15

Arg Leu Tyr Val Asp Phe Pro Gln Arg Leu Arg His Leu Leu Ala Asp
            20                  25                  30

Trp Leu Glu Ser Gln Pro Trp Glu Phe Leu Val Gly Ser Asp Ala Phe
        35                  40                  45

Cys Tyr Asn Met Ala Ser Ala Leu Leu Ser Ala Thr Val Gln Arg Leu
    50                  55                  60

Gln Ala Thr Ala Gly Glu Gln Gly Lys Gly Asn Ser Ile Leu Pro His
65                  70                  75                  80

Ile Ser Thr Leu Glu Ser Ile Tyr Gln Arg Asp Pro Leu Lys Leu Val
                85                  90                  95

Ala Thr Ile Arg Gln Ile Leu Gln Gly Glu Lys Lys Ala Val Ile Glu
            100                 105                 110

Glu Phe Arg His Leu Pro Gly Pro Phe His Arg Lys Gln Glu Glu Leu
        115                 120                 125
```

```
Lys Phe Thr Thr Pro Leu Gly Arg Leu His His Arg Val Arg Glu Thr
    130                 135                 140

Arg Leu Leu Arg Glu Ser Leu His Leu Gly Pro Lys Thr Gly Gln Val
145                 150                 155                 160

Ser Leu Gln Asn Leu Ile Asp Pro Pro Leu Asn Gly Pro Gly Pro Ser
                165                 170                 175

Glu Asp Leu Pro Thr Ile Leu Gln Gly Thr Val Gly Asp Leu Glu Thr
            180                 185                 190

Thr Gln Pro Leu Val Leu Leu Arg Ile Gln Ile Trp Lys Arg Gln Gln
        195                 200                 205

Gln Leu Ala Gly Asn Gly Thr Pro Phe Glu Ser Leu Ala Gly Leu
    210                 215                 220

Gln Glu Arg Cys Glu Ser Leu Val Glu Ile Tyr Ser Gln Leu His Gln
225                 230                 235                 240

Glu Ile Gly Ala Ala Ser Gly Glu Leu Glu Pro Lys Thr Arg Ala Ser
                245                 250                 255

Leu Ile Ser Arg Leu Asp Glu Val Leu Arg Thr Leu Val Thr Ser Ser
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Gln Phe Leu Gly Thr
    290                 295                 300

Ser Thr Lys Pro Pro Met Val Arg Ala Asp Met Val Thr Glu Lys Gln
305                 310                 315                 320

Ala Arg Glu Leu Ser Leu Ser Gln Gly Pro Gly Thr Gly Val Glu Ser
                325                 330                 335

Thr Gly Glu Ile Met Asn Asn Thr Val Pro Leu Glu Asn Ser Ile Pro
            340                 345                 350

Ser Asn Cys Cys Ser Ala Leu Phe Lys Asn Leu Leu Leu Lys Lys Ile
        355                 360                 365

Lys Arg Cys Glu Arg Lys Gly Thr Glu Ser Val Thr Glu Glu Lys Cys
    370                 375                 380

Ala Val Leu Phe Ser Thr Ser Phe Thr Leu Gly Pro Asn Lys Leu Leu
385                 390                 395                 400

Ile Gln Leu Gln Ala Leu Ser Leu Ser Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Gly Glu Arg Val Pro Trp
        435                 440                 445

Glu Lys Met Cys Glu Thr Leu Asn Leu Lys Phe Met Val Glu Val Gly
    450                 455                 460

Thr Ser Arg Gly Leu Leu Pro Glu His Phe Leu Phe Leu Ala Gln Lys
465                 470                 475                 480

Ile Phe Asn Asp Asn Ser Leu Ser Val Glu Ala Phe Gln His Arg Cys
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
    530                 535                 540
```

```
Gln Tyr Val Thr Ser Leu Leu Asn Glu Pro Asp Gly Thr Phe Leu
545                 550                 555                 560

Leu Arg Phe Ser Asp Ser Glu Ile Gly Gly Ile Thr Ile Ala His Val
        565                 570                 575

Ile Arg Gly Gln Asp Gly Ser Ser Gln Ile Glu Asn Ile Gln Pro Phe
                580                 585                 590

Ser Ala Lys Asp Leu Ser Ile Arg Ser Leu Gly Asp Arg Ile Arg Asp
            595                 600                 605

Leu Ala Gln Leu Lys Asn Leu Tyr Pro Lys Lys Pro Lys Asp Glu Ala
        610                 615                 620

Phe Arg Ser His Tyr Lys Pro Glu Gln Met Gly Lys Asp Gly Arg Gly
625                 630                 635                 640

Tyr Val Ser Thr Thr Ile Lys Met Thr Val Glu Arg Asp Gln Pro Leu
                645                 650                 655

Pro Thr Pro Glu Pro Gln Met Pro Ala Met Val Pro Pro Tyr Asp Leu
                660                 665                 670

Gly Met Ala Pro Asp Ala Ser Met Gln Leu Ser Ser Asp Met Gly Tyr
            675                 680                 685

Pro Pro Gln Ser Ile His Ser Phe Gln Ser Leu Glu Glu Ser Met Ser
        690                 695                 700

Val Leu Pro Ser Phe Gln Glu Pro His Leu Gln Met Pro Pro Asn Met
705                 710                 715                 720

Ser Gln Ile Thr Met Pro Phe Asp Gln Pro His Pro Gln Gly Leu Leu
                725                 730                 735

Gln Cys Gln Ser Gln Glu His Ala Val Ser Ser Pro Glu Pro Met Leu
                740                 745                 750

Trp Ser Asp Val Thr Met Val Glu Asp Ser Cys Leu Thr Gln Pro Val
            755                 760                 765

Gly Gly Phe Pro Gln Gly Thr Trp Val Ser Glu Asp Met Tyr Pro Pro
        770                 775                 780

Leu Leu Pro Pro Thr Glu Gln Asp Leu Thr Lys Leu Leu Leu Glu Asn
785                 790                 795                 800

Gln Gly Glu Gly Gly Ser Leu Gly Ser Gln Pro Leu Leu Lys Pro
                805                 810                 815

Ser Pro Tyr Gly Gln Ser Gly Ile Ser Leu Ser His Leu Asp Leu Arg
            820                 825                 830

Thr Asn Pro Ser Trp
        835

<210> SEQ ID NO 12
<211> LENGTH: 3213
<212> TYPE: DNA
<213> ORGANISM: Mus musculus

<400> SEQUENCE: 12
gccgctctaa cgcaacacgc cctctgtcgg caggtaattg cactgcccgg tctcacctaa      60
ctatgcacgt aaacaatcct cactcgggac gaactgggtt gtgcacgctg gacctgggca     120
agaggaaacc accccaggcc caggtccggg ctcaagcccg cccgattgtc agaagagaac     180
cgctggacag acctcagac ccatggggct tggtagtgcc ctctgagaga gggagaagat      240
agcagcgggg ctgccgaggc accctgtata tcccagatca tgtctctgtg gggcctaatt     300
tccaagatgt cccagaaaaa actgcaacgg ctctatgttg actttccaca acgcctacgg     360
catctcctgg ctgactggct ggagagccag ccctgggagt tcctggtcgg ttcagatgct     420
```

```
ttctgttaca acatggccag tgccctactt tctgccaccg tccagcgtct tcaggccact    480
gctggagagc aggggaaggg aaacagcatc ttgccgcaca tcagcacctt ggagagcatc    540
tatcagaggg accccctgaa gctggtggcc accatcagac aaatacttca agggagaaa    600
aaagctgtta tagaagagtt ccgccacctg ccagggccct tccatcggaa gcaggaagaa    660
ctcaagttta ctacacccct cggaaggctt caccatcgag taaggagac ccggcttctc    720
cgagaatctc tacacctagg gcctaagact ggacaagtgt ctctgcagaa tttgatagac    780
cctcctctca atggtcctgg tccaagtgag gacctgccca ccatactcca ggggactgtg    840
ggggacctgg agaccaccca gcccctggtt ctgttaagga ttcagatttg gaagcggcag    900
caacagctgg cagggaatgg cacacccttt gaggagagcc tagcagggct ccaggagagg    960
tgtgaaagcc tggtggaaat ttattcccag ctccaccagg agattggggc agccagtggg   1020
gaactggaac ccaagacccg ggcatcgctg ataagccgtc tggatgaagt cctgcgaacc   1080
cttgtgacca gctcttttcct ggtggagaag cagcccccc aggttctgaa gacacagact   1140
aagttccagg ctggggttcg attcctgctg ggtctgcagt ttctagggac ctcaaccaag   1200
cctccaatgg tcagagctga catggtgaca gagaaacagg ccagagaact aagtctgtcc   1260
caggggcccg ggactggagt ggagagcaca ggagagatca tgaacaacac ggtgcccctg   1320
gagaacagca ttcccagcaa ctgctgctcc gccctgttca agaacctgct cctgaagaaa   1380
ataaagcgct gtgagcggaa gggcacagag tctgtcaccg aggagaagtg tgctgtgctc   1440
ttctccacga gcttcacatt gggccccaac aaacttctca tccagcttca ggccctgtct   1500
ctgtccttgg tggtcatcgt gcatggtaac caagacaaca acgccaaagc taccatccta   1560
tgggacaatg ccttctctga gatggaccga gtgccctttg tggtgggtga gcgagtgccc   1620
tgggagaaga tgtgtgaaac cctaaacctc aagtttatgg ttgaggtggg gaccagccgg   1680
ggactgcttc cagagcactt cctgttcctc gcccagaaga tcttcaacga caacagcctc   1740
agtgtggagg cctttcagca ccgctgtgtg tcctggtcac agttcaataa ggagatcctg   1800
ctgggccgag gcttcacatt tttggcagtgg tttgatggtg tcctggacct caccaaacgc   1860
tgtctccgga gctactggtc agatcggctg atcattggct ttattagtaa gcaatatgtc   1920
actagccttc tcctcaatga gccagatggg accttcctcc tccgctttag cgactctgag   1980
atcgggggca tcaccattgc acacgtcatc cggggtcagg atggctcctc acagatagag   2040
aacatccagc cattttctgc caaagacctg tccattcgct cactggggga ccggatccgg   2100
gatcttgctc agttaaaaaa cctctacccc aagaaaccca agatgaggc tttccggagt   2160
cactataagc ccgaacagat ggggaaggac gggaggggtt atgtctctac tactatcaag   2220
atgactgtgg aaagggacca gccccttcct actccagagc cccagatgcc tgccatggtg   2280
ccaccttatg atcttggaat ggcccctgat gcttccatgc aactcagctc agatatgggg   2340
tatcctccac agtccatcca ctcatttcag agcctagaag agtccatgag tgtactgcca   2400
tcttttcagg agcctcacct gcaaatgccc cccaacatga gccagataac catgccccttt   2460
gaccagcctc accccaggg tctgctgcag tgccagtccc aggaacatgc tgtgtccagc   2520
cctgaaccca tgctttggtc agatgtgact atggtagagg acagttgcct aactcagcct   2580
gtgggaggtt tccccaagg cacctgggtc agtgaagaca tgtaccctcc cctgctgcct   2640
cccactgaac aggacctcac caagcttctc ctggagaacc aaggggaggg aggagggtcc   2700
ttaggaagcc agcccctcct gaaaccatct ccttatgggc aatcaggat ctcactgtcc   2760
cacctggacc taaggaccaa ccccagctgg tgatcccagc tggagaagcc cagaaacaaa   2820
```

-continued

```
gcctcttctg tctctatgga ccagctctgg acacctgctc atgcaggtgc cttccgtctc   2880
aactgttcct tggttaagag aaaagaactg gctgggagac catgtggtgt atggaactgc   2940
tgtgctctgt cctacctgcc atatcagggc ccccttttc cagcactggg tgcaaaggga    3000
tgagtggggt gttaatgctc gaatgtgata caactgtatc acaacacaca cgcacacaca   3060
tacacacaca ccagaactgt gttgagccag ggcctgggac tcaacataca gaaacataga   3120
gacattgtgc ccaaagacag aggacatata gccctagggc attgaagctg ggctcagtga   3180
ctctgggagg gagaaaaagg aaaaagtggg tat                                3213
```

<210> SEQ ID NO 13
<211> LENGTH: 813
<212> TYPE: PRT
<213> ORGANISM: Rattus norvegicus

<400> SEQUENCE: 13

```
Met Ser Leu Trp Ser Leu Val Ser Lys Met Ser Pro Glu Lys Leu Gln
1               5                   10                  15

Arg Leu Tyr Val Asp Phe Pro Gln His Leu Arg His Leu Leu Ala Glu
                20                  25                  30

Trp Leu Glu Asn Gln Pro Trp Glu Phe Leu Val Gly Ser Asp Ala Phe
            35                  40                  45

Cys Tyr Asn Met Ala Ser Ala Leu Leu Ser Ala Thr Val Gln Arg Leu
        50                  55                  60

Gln Ala Ser Ala Gly Glu Gln Gly Lys Gly Ser Ser Leu Leu Gln His
65                  70                  75                  80

Ile Ser Thr Leu Glu Ser Ile Tyr Gln Arg Asp Pro Leu Lys Leu Val
                85                  90                  95

Ala Thr Ile Arg Gln Ile Leu Gln Gly Glu Lys Lys Ala Val Ile Glu
            100                 105                 110

Glu Phe His His Leu Pro Gly Pro Phe His Arg Lys Gln Glu Glu Leu
        115                 120                 125

Lys Phe Thr Thr Ala Leu Gly Arg Leu Gln His Arg Val Arg Glu Thr
    130                 135                 140

Arg Ile Leu Arg Glu Ser Leu Gln Gln Gly Thr Lys Thr Ala Gln Val
145                 150                 155                 160

Ser Leu Lys Asn Leu Ile Asp Pro Pro Ala Asn Gly Thr Gly Pro Ser
                165                 170                 175

Glu Asp Leu Ala Thr Met Leu Gln Gly Thr Val Gly Asp Leu Glu Ala
            180                 185                 190

Thr Gln Ala Leu Val Leu Lys Arg Ile Gln Ile Trp Lys Arg Gln Gln
        195                 200                 205

Gln Leu Ala Gly Asn Gly Thr Pro Phe Glu Glu Ser Leu Ala Gly Leu
    210                 215                 220

Gln Glu Arg Cys Glu Ser Leu Val Glu Ile Tyr Ser Gln Leu Gln Gln
225                 230                 235                 240

Glu Ile Gly Ala Ala Ser Gly Glu Leu Glu Pro Lys Thr Arg Ala Ser
                245                 250                 255

Leu Ile Ser Arg Leu Asp Glu Val Leu Arg Thr Leu Val Thr Ser Ser
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Gln Phe Leu Gly Thr
    290                 295                 300
```

```
Ser Ala Lys Pro Pro Leu Val Arg Ala Asp Met Val Thr Glu Lys Gln
305                 310                 315                 320

Ala Arg Glu Leu Ser Leu Pro Gln Gly Ser Gly Ala Gly Val Glu Ser
                325                 330                 335

Thr Gly Glu Ile Met Asn Asn Thr Val Pro Leu Glu Asn Ser Val Pro
            340                 345                 350

Gly Asn Cys Cys Ser Ala Leu Phe Lys Asn Leu Leu Leu Lys Lys Ile
                355                 360                 365

Lys Arg Cys Glu Arg Lys Gly Thr Glu Ser Val Thr Glu Glu Lys Cys
        370                 375                 380

Ala Val Leu Phe Ser Thr Ser Phe Met Leu Gly Pro Asn Lys His Leu
385                 390                 395                 400

Ile Gln Leu Gln Ala Leu Ser Leu Pro Leu Val Ile Val His Gly
                405                 410                 415

Asn Gln Asp Asn Asn Ala Lys Ala Thr Ile Leu Trp Asp Asn Ala Phe
                420                 425                 430

Ser Glu Met Asp Arg Val Pro Phe Val Val Ala Glu Arg Val Pro Trp
            435                 440                 445

Glu Lys Met Cys Glu Thr Leu Asn Leu Lys Phe Met Ala Glu Val Gly
        450                 455                 460

Thr Ser Arg Gly Leu Leu Pro Glu His Phe Leu Phe Leu Ala Gln Lys
465                 470                 475                 480

Ile Phe Asn Asp Asn Ser Leu Ser Ile Glu Ala Phe Gln His Arg Cys
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
                530                 535                 540

Gln Tyr Val Thr Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575

Ile Arg Gly Gln Asp Gly Ser Ser Gln Ile Glu Asn Ile Gln Pro Phe
            580                 585                 590

Ser Ala Lys Asp Leu Ser Ile Arg Ser Leu Gly Asp Arg Ile Arg Asp
        595                 600                 605

Leu Ala Gln Leu Lys Asn Leu Tyr Pro Lys Lys Pro Lys Asp Glu Ala
610                 615                 620

Phe Arg Ser His Tyr Lys Pro Glu Gln Met Gly Lys Asp Gly Arg Gly
625                 630                 635                 640

Tyr Val Ser Thr Thr Ile Lys Met Thr Val Glu Arg Asp Gln Pro Leu
                645                 650                 655

Pro Thr Pro Glu Pro Gln Met Pro Ala Met Val Ala Pro Tyr Asp Leu
            660                 665                 670

Gly Met Ala Pro Asp Ala Ser Met Gln Leu Ser Ser Asp Met Val Pro
        675                 680                 685

His Leu Gln Met Pro Pro Thr Met Ser Gln Ile Ser Met Pro Phe Asp
            690                 695                 700

Gln Pro His Pro Gln Gly Leu Leu Gln Cys Gln Ser Gln Glu His Ala
705                 710                 715                 720
```

```
Val Ser Ser Pro Glu Pro Leu Leu Cys Ser Asp Val Thr Met Ala Glu
                725                 730                 735

Asp Ser Cys Leu Thr Gln Pro Val Gln Gly Phe Pro Gln Gly Thr Trp
            740                 745                 750

Val Ser Glu Gly Met Tyr Pro Pro Leu Met Pro Pro Thr Glu Gln Asp
        755                 760                 765

Leu Thr Lys Leu Leu Leu Glu Gly Gln Gly Glu Gly Gly Ser Ile
    770                 775                 780

Gly Thr Gln Pro Leu Leu Gln Pro Ser Ser Tyr Gly Gln Ser Gly Ile
785                 790                 795                 800

Ser Met Ser His Leu Asp Leu Arg Thr Asn Pro Ser Trp
                805                 810

<210> SEQ ID NO 14
<211> LENGTH: 2442
<212> TYPE: DNA
<213> ORGANISM: Rattus norvegicus

<400> SEQUENCE: 14
atgtctctgt ggagtctagt ttccaagatg tccccagaaa aactgcaacg gctctatgtt    60
gactttccac aacacctgcg gcatcttctg ccgaatggc tggagaatca gccctgggag   120
ttcctggttg gttcagatgc tttctgttac aacatggcta gtgccctact ttctgccact   180
gtccagcgtc ttcaggcctc tgcaggagag caggggaaag gaagcagcct cttgcagcac   240
atcagcacct ggagagcat ctatcagagg accccctga agctggtggc caccatcaga   300
caaatacttc aaggggagaa aaaagctgtt atagaagagt tccaccacct gccagggccc   360
ttccatcgaa agcaggaaga actcaagttt actacagccc tgggcaggct tcagcaccga   420
gtaagggaga ccaggattct ccgagaatct ctgcagcagg ggaccaagac tgcgcaagtg   480
tctctgaaga acttgataga ccctcctgcc aatggcactg gtccaagtga ggatctggcc   540
acgatgctgc aggggactgt gggggacttg gaggccaccc aggctctagt gctgaaaagg   600
attcagattt ggaagcggca acagcagctg cagggaatg gcacacccct tgaggagagc   660
ctggcagggc tgcaggagag gtgtgaaagc ctggtggaaa tttattccca gctgcagcag   720
gagattggag cagccagtgg ggagcttgag cccaagaccc gggcatcgct cataagccgt   780
ctggatgaag tcctgcgaac cctcgtgacc agctctttcc tggtggagaa gcagccccca   840
caggttctga gacacagac taagtttcag gctggggttc gattcctact gggtctgcag   900
ttcctaggga cctcagccaa gcctccactg gtcagagctg acatggtgac agagaaacag   960
gccagagaac taagcctgcc ccaggggtct ggggctggag tggagagcac aggagagatc  1020
atgaacaata ctgtacctct ggagaacagt gttcctggga actgctgctc tgccctcttc  1080
aagaacctgc tcctgaagaa atcaagcgc tgtgagcgga agggtacaga gtctgtcacc  1140
gaagagaagt gcgctgtgct cttctctacg agcttcatgc tgggcccaa caaacacctc  1200
atccagcttc aggccctgtc tctgcccttg gtggtcatcg ttcatggcaa ccaagacaac  1260
aatgccaaag ctaccatcct gtgggataat gccttctctg agatggaccg agtgcccttt  1320
gtggtagctg agcgagtgcc ctgggagaaa atgtgtgaaa ctctgaacct caagtttatg  1380
gctgaggtgg ggaccagccg gggactgcta ccagaacact tcctgttcct ggcccagaag  1440
atcttcaatg acaacagcct tagcatagag gcctttcagc accgctgtgt gtcttggtca  1500
cagttcaaca aggagattct actgggccga ggcttcactt tttggcagtg gtttgatggt  1560
gtcctggacc tcactaaacg ctgtcttcgg agctactggt cagatcggct gatcatcggc  1620
```

-continued

```
tttatcagta agcaatatgt cactagcctt ctcctcaacg agccagatgg aaccttcctc    1680
ctccgcttta gcgactctga gattgggggc atcaccattg cccatgtcat ccggggtcag    1740
gatggctcct cacagataga aacatccag ccgttttctg ccaaagacct atccattcgc     1800
tcactggggg accgaatccg agatcttgct caattaaaaa acctctaccc caagaaaccc    1860
aaggatgagg cttttcggag ccactataag ccggaacaga tgggaaagga cgggaggggt    1920
tatgtctcaa ctactatcaa gatgactgtg gaaagggacc agccccttcc tactccagag    1980
ccccagatgc ctgccatggt ggcccttat gatcttggaa tggcccctga tgcttccatg      2040
caactcagct cagatatggt gcctcacctt caaatgcccc ccaccatgag ccagataagc     2100
atgccctttg accagcctca tccccagggc ctgctccagt gccagtccca ggagcatgcg    2160
gtgtccagcc ctgaacccctt gctgtgttca gatgtcacta tggcggaaga cagctgccta    2220
actcagcctg tgcaaggttt cccccagggc acctgggtca gcgaaggcat gtaccctccc    2280
ctgatgcctc ccactgaaca ggacctcacc aagcttctcc tagagggcca aggggaaggt     2340
ggaggatcca tagggactca gcccctcctg caaccatctt cttatgggca atcggggatc    2400
tcaatgtccc acctggacct aaggaccaac cccagttggt ga                       2442

<210> SEQ ID NO 15
<211> LENGTH: 21
<212> TYPE: DNA
<213> ORGANISM: Homo sapiens

<400> SEQUENCE: 15
aagcaggaag aactcaagtt t                                                 21

<210> SEQ ID NO 16
<211> LENGTH: 21
<212> TYPE: DNA
<213> ORGANISM: Homo sapiens

<400> SEQUENCE: 16
aaacagtacg ttactagcct t                                                 21

<210> SEQ ID NO 17
<211> LENGTH: 21
<212> TYPE: DNA
<213> ORGANISM: Homo sapiens

<400> SEQUENCE: 17
aagaatcagt caacgtgttg t                                                 21

<210> SEQ ID NO 18
<211> LENGTH: 21
<212> TYPE: DNA
<213> ORGANISM: Homo sapiens

<400> SEQUENCE: 18
aaagcactgg agaaatcatc a                                                 21

<210> SEQ ID NO 19
<211> LENGTH: 21
<212> TYPE: DNA
<213> ORGANISM: Artificial sequence
<220> FEATURE:
<223> OTHER INFORMATION: siRNA

<400> SEQUENCE: 19
```

```
aaacuugagu ucuuccugct t                                          21

<210> SEQ ID NO 20
<211> LENGTH: 21
<212> TYPE: DNA
<213> ORGANISM: Artificial sequence
<220> FEATURE:
<223> OTHER INFORMATION: siRNA

<400> SEQUENCE: 20
aaggcuagua acguacugut t                                          21

<210> SEQ ID NO 21
<211> LENGTH: 21
<212> TYPE: DNA
<213> ORGANISM: Artificial sequence
<220> FEATURE:
<223> OTHER INFORMATION: siRNA

<400> SEQUENCE: 21
acaacacguu gacugauuct t                                          21

<210> SEQ ID NO 22
<211> LENGTH: 21
<212> TYPE: DNA
<213> ORGANISM: Artificial sequence
<220> FEATURE:
<223> OTHER INFORMATION: siRNA

<400> SEQUENCE: 22
ugaugauuuc uccagugcut t                                          21
```

MATERIALS AND METHODS FOR TREATMENT OF ALLERGIC DISEASE

FIELD OF THE INVENTION

The present invention relates to materials and methods for the treatment of allergic disease, and particularly although not exclusively, to nucleic acids for use in repressing the expression of cellular STAT6 ribonucleic acid, peptide, polypeptide or protein.

BACKGROUND TO THE INVENTION

The incidence and cost of treating respiratory tract allergic disease is increasing. Cost-efficient, more effective, or preventative therapeutics are therefore desirable[1].

One such allergic disease is asthma in which the inflammatory pathology is predominantly mediated by cytokines which utilise a common intra-cellular transcription factor known as STAT6 (signal transducer and activator of transcription 6). STAT6 is critical for allergy development, mucosal/airway inflammation and asthma (STAT6-deficient animals do not get asthma, even when challenged in a way that induces asthma in normal mice).

Drugs that specifically and effectively target STAT6, which resides and operates in the intracellular environment, have proved difficult to develop. For example, anti-STAT6 peptides have been investigated[13] but were found to achieve only limited and very transient (minutes) repression of STAT6 protein expression. The transient effect is considered to be due to peptide degradation by endogenous cellular proteases.

Attempts to repress STAT6 expression in vivo through antisense DNA techniques[15] have proved unsuccessful. This approach suffers from a series of problems. For example only a low inhibition of STAT6 expression is obtained, even at high concentrations of antisense DNA, the effects are transient and the antisense molecule is subject to degradation and is difficult to target to the appropriate intracellular location. The high concentration of antisense DNA required to produce any useful effect often causes the antisense DNA to exhibit antigenic properties and can invoke an immune response. Furthermore, mice treated with STAT6 directed antisense DNA did not exhibit an improvement in allergic symptoms and developed splenomegaly[16], i.e. a toxic side effect.

Accordingly, to date, STAT6 has proved to be a very difficult molecule to effectively inhibit or repress in a therapeutically useful manner. Despite several attempts, no successful drug or composition has been developed that targets STAT6 effectively without causing non-specific side-effects.

STAT6

STAT6 is the Signal Transducer and Activator of Transcription 6. To be functional in intact cells, STAT6 has to be phosphorylated. Sequence data for human STAT6 can be accessed from NCBI (www.ncbi.nlm.nih.gov) under accession numbers NP_003144 (NM_003153) and U16031.

RNA INTERFERENCE (RNAi)

RNAi utilises small double-stranded RNA molecules (dsRNA) to target messenger RNA (mRNA), the precursor molecule that cells use to translate the genetic code into functional proteins. During the natural process of RNAi, dsRNA is enzymatically processed into short-interfering RNA (siRNA) duplexes of 21 nucleotides in length. The antisense strand of the siRNA duplex is then incorporated into a cytoplasmic complex of proteins (RNA-induced silencing complex or RISC). The RISC complex containing the antisense siRNA strand also binds mRNA which has a sequence complementary to the antisense strand—allowing complementary base-pairing between the antisense siRNA strand and the sense mRNA molecule. The mRNA molecule is then specifically cleaved by an enzyme (RNase) associated with the RISC resulting in specific gene silencing[3,4]. For gene silencing (i.e. mRNA cleavage) to occur, anti-sense RNA (i.e. siRNA) has to become incorporated into the RISC. This is a natural and highly efficient process that occurs in all nucleated cells and whose origin is thought to be in mediating protection from transposable elements (e.g. viruses) and in normal regulation of gene expression. It is therefore distinct from the artificial process of introducing anti-sense DNA molecules into cells, where targeting of mRNA occurs through simple base-pairing of the naked anti-sense DNA molecule to its RNA target.

The advantages of RNAi over other gene-targeting strategies such as DNA anti-sense oligonucleotides can include its relative specificity, its enhanced efficacy, and the fact that siRNA treatment feeds into a natural RNAi pathway that is inherent to all cells.

However, the success of RNAi in gene repression or silencing is unpredictable, indeed the outcome can be highly variable and may depend on a variety of factors which include the accessibility of the genetic target (i.e. mRNA) and the efficiency of RNAi in the cell type being targeted.

SUMMARY OF THE INVENTION

The inventors have designed and in vitro tested STAT6 siRNA (short interfering RNA). Despite the intrinsic unpredictability of the efficacy of this approach they obtained specific and highly efficient inhibition of the expression of STAT6 mRNA and protein in cell types found in lung tissue, indicating that these molecules will provide effective and specific targeting of STAT6 in vivo.

The evidence presented herein demonstrates that STAT6 siRNA, when transferred into cells by cationic lipid-mediated transfer, are indeed functional and efficiently inhibit STAT6 mRNA, and protein expression without obvious side-effects in human cells.

By targeting these siRNA to representative cells from human airways, the inventors have provided the basis of a new therapeutic treatment for allergic disease of the respiratory tract such as rhinitis and asthma. Non-atopic asthma may also be amenable to STAT6 siRNA therapy. In particular, STAT6 siRNA's may be used to treat the local cells of the respiratory tract via delivery systems such as liposomes or in aerosol form by a standard nebuliser device.

The siRNA's provided specifically and efficiently target STAT6 in that they reduce STAT6 gene expression by >90%. Furthermore, cells treated with STAT6-specific siRNA do not express detectable STAT6 protein expression and they do not exhibit phosphorylation of STAT6 protein in response to physiological stimulus with interleukin-4—in other words, cells treated with individual STAT6 siRNA lose their ability to signal through an intracellular pathway that is heavily implicated in the development of allergic immune responses and associated diseases of the respiratory tract that include asthma and allergic rhinitis.

The inventors have also demonstrated that STAT6 targeted siRNA provide persistent inhibition of STAT6 expression in lung cells at low (nanomolar, nM) concentrations of siRNA. Furthermore, inhibition of functional STAT6 protein is achieved without induction of an interferon response. This response is often seen when long (>30 bp) double stranded RNA is introduced into mammalian cells—the interferon response occurs naturally in response to viruses which harbour dsRNA, resulting in non-specific suppression of cellular gene expression. The fact that no such response is seen in the target cell group is further indicative of the efficacy of the siRNA approach taken by the inventors.

The inventors have demonstrated that STAT6 targeted siRNA provide potent, non-toxic, inhibitors of STAT6 function at very low concentration.

Treatment of allergic inflammation of the respiratory tract may be achieved by taking advantage of nebulisers or nasal sprays to deliver STAT6 siRNA. These delivery methods are already standard in conventional treatments. Furthermore, for asthma or rhinitis, delivery of siRNA may take advantage of available commercial formulations (e.g. Smarticles®, Novosom AG, Germany) in aerosol or liquid form.

At its most general the present invention relates to nucleic acids, particularly siRNA, and their uses in repressing or silencing the expression of nucleic acids, peptides, polypeptides or protein.

More particularly, the present invention relates to the repression of STAT 6 ribonucleic acid (e.g. mRNA), peptide, polypeptide or protein expression. Ribonucleic acids, particularly in the form of siRNA, are provided having substantial sequence identity or complementarity along their length to all or a portion or fragment of at least one RNA sequence coding for a STAT6 protein. Such RNA sequences may include an RNA sequence (e.g. mRNA) encoding a STAT6 protein (e.g. the protein encoded by one of amino acid sequences SEQ ID Nos. 9, 11 or 13) or one of the RNA sequences encoded by one of SEQ ID Nos. 10, 12 or 14.

The use of such ribonucleic acids (siRNA) in the treatment of respiratory tract allergic or non-allergic disease, e.g. asthma or rhinitis, and in the manufacture of a medicament for the treatment of respiratory tract allergic or non-allergic diseases together with methods of treating respiratory tract allergic or non-allergic diseases are also provided.

The inventors have also provided methods of repressing or silencing the expression of a STAT6 ribonucleic acid (mRNA) or protein in vitro and cells in which STAT6 ribonucleic acid or protein expression is repressed and which may be obtainable by such methods.

In one aspect of the invention a ribonucleic acid, particularly double stranded siRNA, is provided for use in the treatment of respiratory tract allergic disease in an individual.

The ribonucleic acid (siRNA) preferably represses the expression of STAT6 ribonucleic acid (mRNA), polypeptide or protein. Preferably STAT6 ribonucleic acid (mRNA) or protein function is also repressed.

Nucleic acids according to the invention may be DNA or RNA and may be single or double stranded. Preferably the nucleic acid is an RNA and is double stranded.

Preferred nucleic acids include RNA molecules having a sequence of, or complementary to, any of SEQ ID Nos. 1-8 and nucleic acids having a sequence identity of at least 60% to one of SEQ ID Nos. 1-8 or a complementary sequence thereof, and more preferably having at least 70, 80, 85, 90, 95% or 100% sequence identity. DNA molecules encoding RNA's comprising these sequences are also provided.

Isolated nucleic acids which may include an RNA molecule having a sequence of, or complementary to, any of SEQ ID Nos. 1-8, nucleic acids having a sequence identity of at least 60% to one of SEQ ID Nos. 1-8 or a complementary sequence thereof, and more preferably having at least 70, 80, 85, 90, 95 or 100% sequence identity, and DNA molecules encoding RNA's comprising these sequences form another aspect of the invention.

In a further aspect of the invention the nucleic acids described, e.g. double stranded siRNA, are provided for use in the manufacture of a medicament for the treatment of respiratory tract allergic or non-allergic disease, e.g. asthma or rhinitis. Preferably the mechanism of treatment comprises the repression of expression of a STAT6 ribonucleic acid (mRNA) and/or protein in vivo.

In yet a further aspect of the invention a method of treating respiratory tract allergic disease in an individual in need of such treatment is provided. The method may comprise the step of administering to the individual an amount of one or more of the ribonucleic acids described herein, e.g. siRNA, which is effective to treat the symptoms of these disorders.

The individual to be treated may be a patient in need of treatment. The patient may be any animal or human. The patient may be a non-human mammal (e.g. mouse, rat or other mammal from the order Rodentia), but is more preferably a human patient. The patient may be male or female.

Medicaments and pharmaceutical compositions according to aspects of the present invention may be formulated for administration by a number of routes, including but not limited to, parenteral, intravenous, intramuscular, intratumoural, oral, oral inhalation and nasal. The medicaments and compositions may be formulated in fluid or solid form. Fluid formulations may be formulated for administration by injection to a selected region of the human or animal body. Fluid formulations may be provided which are capable of being administered by aerosol.

In another aspect of the invention, a method is provided for repressing or silencing the cellular expression of STAT6 ribonucleic acid (mRNA) or protein in vitro. The method may comprise the contacting of a cell or cells with a nucleic acid described herein, e.g. a ribonucleic acid such as an siRNA, to deliver the nucleic acid (e.g. siRNA) to the cell(s). In one arrangement the nucleic acid (e.g. siRNA) may be complexed with a carrier, e.g. a lipophilic carrier to assist and/or enhance passage of the nucleic acid across the cell membrane.

Accordingly, cells may be provided in which the expression of STAT6 ribonucleic acid (mRNA) or protein is repressed or silenced.

Suitable cells may be selected from human cells, or alternatively from non-human cells, preferably rat, mouse or other rodent (including cells from any animal in the order Rodentia). Other suitable non-human cells may be e.g., from pig, sheep, non-human primate or other non-human vertebrate organism and/or non-human mammalian cells.

Ribonucleic acids of the invention may be prepared as part of a pharmaceutical composition comprising a carrier, e.g. a lipophilic carrier or vesicle, or adjuvant in addition to the nucleic acid. Pharmaceutical compositions and medicaments of the invention may be formulated for oral inhalation or nasal administration, alternatively for parenteral, intravenous or intramuscular administration.

For the treatment of respiratory tract allergy, suitable medicaments or therapeutics include those suitable for nasal and/or oral administration (preferably by inhalation) and may be provided as a solution suitable for generation of aerosolised droplets of the medicament for delivery to the airways and lungs by use of an appropriate nebuliser or inhaler. Compositions and medicaments according to the present invention may be formulated for delivery to the respiratory tract, e.g. intranasally, inhalationally or orally. Such compositions and medicaments may comprise suitable siRNA molecules with or without a suitable transfection reagent[9].

A number of transfection reagents suitable for in vivo delivery of siRNA molecules are known to the person skilled in the art[10]. Examples of such agents include lipophilic agents such as liposomes or commercially available agents such as Neophectin™ (Neopharm) and Smarticles® (Novosom AG).

Pulmonary surfactant may also be used to deliver siRNA into the lungs. Pulmonary surfactants are commercially available (e.g. CuroSurf™) and are advantageous in that they are already clinically established and validated for safe use in humans.

According to one aspect of the present invention there is provided an isolated double stranded short interfering ribonucleic acid (siRNA) molecule that represses or silences expression of STAT6 nucleic acid (e.g. a STAT6 ribonucleic acid such as mRNA) or protein.

The sense strand of the siRNA may comprises a contiguous nucleotide sequence, wherein the base sequence of the sense strand has at least 70% sequence identity to the base sequence of a contiguous nucleotide sequence of corresponding length which is contained in (i.e. is embedded within, or is a part, all or a fragment of) the mRNA sequence encoded by one of the human, mouse or rat STAT6 nucleotide sequences (SEQ ID Nos. 10, 12 or 14). The contiguous nucleotide sequence of corresponding length contained in the mRNA sequence may be the RNA sequence of any one of SEQ ID Nos. 5-8 or the RNA sequence encoded by any one of SEQ ID Nos. 15-18.

The antisense strand of the siRNA may comprise a contiguous nucleotide sequence, wherein the base sequence of the antisense strand has at least 70% sequence complementarity to the base sequence of a contiguous nucleotide sequence of corresponding length which is contained in (i.e. is embedded within, or is a part, all or a fragment of) the mRNA sequence encoded by one of the human, mouse or rat STAT6 nucleotide sequences (SEQ ID Nos. 10, 12 or 14). The contiguous nucleotide sequence of corresponding length contained in the mRNA sequence may be the RNA sequence of any one of SEQ ID Nos. 5-8 or the RNA sequence encoded by any one of SEQ ID Nos. 15-18.

The specified degree of sequence identity or complementarity may be at least 80%, 90%, 95%, 96%, 97%, 98%, 99% or 100%.

The anti-sense strand may be entirely complementary to said sense strand. The sense and antisense strands may be of the same length or of different lengths. Each strand may have a length in the range of 10 to 30 nucleotides, 15 to 25 nucleotides or 18 to 23 nucleotides. More preferably, each strand may have a length which is one of 19, 20, 21 or 22 nucleotides.

siRNA according to the present invention may have an antisense strand that hybridises to the mRNA encoded by one of SEQ ID Nos. 10, 12 or 14 under high or very high stringency conditions.

Similarly, siRNA according to the present invention may have a sense strand that hybridises to one of SEQ ID No.s 10, 12 or 14 under high or very high stringency conditions.

In one arrangement, the sense or antisense strand may hybridise to the corresponding other strand of one of SEQ ID Nos. 1-4 under high or very high stringency conditions.

In another arrangement the siRNA may have a sequence identity of at least 70% to the corresponding strand of any one of SEQ ID Nos. 1-4.

In yet another arrangement the antisense strand may have at least 70% sequence complementarity over the entire length of said siRNA to a portion or fragment of RNA sequence coding for a STAT6 protein. In yet a further arrangement the sense strand may have at least 70% sequence identity over the entire length of said siRNA to a portion or fragment of a STAT6 mRNA. The RNA (or mRNA) sequence may be that encoded by any one of SEQ ID Nos. 10, 12 or 14.

siRNA according to the present invention may comprise, or consist of, any one of SEQ ID Nos. 1, 2, 3 or 4.

Preferred siRNA act to repress the function and/or expression of STAT6 mRNA and/or STAT6 protein. siRNA according to the present invention may be provided for use in the treatment of respiratory tract allergic or non-allergic disease. Pharmaceutical compositions comprising siRNA according to the present invention are also provided. Suitable pharmaceutical compositions may be formulated for oral or nasal administration and may comprise a pharmaceutically acceptable diluent, carrier or adjuvant. One type of suitable carrier is a lipophilic carrier or vesicle.

In a further aspect of the present invention siRNA according to the present invention are provided for use in the manufacture of a medicament for the treatment of respiratory tract allergic disease or in non-atopic asthma. The medicament may be formulated for oral or nasal administration.

In yet a further aspect of the present invention a method of treating allergic or non-allergic disease in a patient in need of such treatment is provided, the method comprising the steps of administering to the patient an siRNA or pharmaceutical composition according to the present invention. Suitable pharmaceutical compositions may be formulated for oral or nasal administration.

The siRNA, pharmaceutical compositions, uses and methods of treatment forming part of the present invention may be useful in treating respiratory tract allergic or non-allergic disease. That allergic disease may be asthma or rhinitis. Non-allergic diseases may include non-atopic asthma.

In yet a further aspect of the present invention there is provided a method for repressing the cellular expression of STAT6 protein in vitro comprising, in vitro, contacting a cell with an siRNA according to the present invention.

In yet another aspect of the present invention there is provided a cell, in vitro, in which STAT6 protein or ribonucleic acid expression or function is repressed or silenced. The cell preferably comprises an siRNA according to the present invention.

Suitable cells may comprise mammalian cells (including non-human mammalian cells) or human cells and may be cells from the respiratory tract or the progeny of cells from the respiratory tract, e.g. human bronchial epithelial cells. Components of the respiratory tract may include the trachea, lungs, bronchi or alveoli.

Nucleic acids of the invention may include any of the following double or single stranded RNA sequences.

| | Sequence ID No. |
|---|---|
| 5'-GCAGGAAGAACUCAAGUUUtt-3'<br>3'-ttCGUCCUUCUUGAGUUCAAA-5' | 1 |
| 5'-ACAGUACGUUACUAGCCUUtt-3'<br>3'-ttUGUCAUGCAAUGAUCGGAA-5' | 2 |
| 5'-GAAUCAGUCAACGUGUUGUtt-3'<br>3'-ttCUUAGUCAGUUGCACAACA-5 | 3 |
| 5'-AGCACUGGAGAAAUCAUCAtt-3'<br>3'-ttUCGUGACCUCUUUAGUAGU-5' | 4 |
| GCAGGAAGAACUCAAGUUU | 5 |
| ACAGUACGUUACUAGCCUU | 6 |
| GAAUCAGUCAACGUGUUGU | 7 |
| AGCACUGGAGAAAUCAUCA | 8 |

Furthermore, ribonucleic acids of the invention may comprise ribonucleic acid molecules which hybridise with any of SEQ ID Nos. 1 to 8 under very high, high or intermediate stringency conditions.

siRNA molecules of the present invention may be designed using the sequence information for STAT6 ribonucleic acid and protein that is available in the art. FIGS. 4 to 6 provide nucleotide sequence information for the STAT6 gene of human, mouse and rat. From such a nucleotide sequence it is possible to design an siRNA molecule which specifically targets the expression and/or function of STAT6. For example, one can design and synthesise an siRNA molecule which has an antisense strand composed of a sequence of nucleotides complementary to a fragment of an RNA encoded by one of SEQ ID No.'s 10, 12 or 14, which RNA fragment may be encoded by a corresponding DNA fragment starting at any selected nucleotide of any one of SEQ ID Nos. 10, 12 or 14. The complementary sense strand can also be readily designed and synthesised in order to provide a double stranded STAT6 siRNA.

siRNA molecules of the invention may be designed to optionally incorporate, as part of the siRNA, two contiguous thymine bases at the 3' end of one or each strand of the siRNA molecule. These thymine bases preferably "overhang" the 5' end of the opposing strand. These thymine bases are preferably part of (or are encoded by) the natural DNA or RNA sequence which the sense or antisense strand of the siRNA is based on. Alternatively they may be deliberately incorporated during synthesis of the siRNA.

siRNA molecules of the invention may be of any length, but preferred nucleic acids are small and may have a strand length of at least 10 nucleotides and no more than 50 nucleotides. Particularly suitable siRNA will have a strand length in the range 10 to 30 nucleotides and more suitably in the range 15 to 25 nucleotides. Selected siRNA may have a strand length of any one of 15, 16, 17, 18, 19, 20, 21, 22, 23, 24 or 25 nucleotides in length. For a double stranded siRNA having a strand length of, say, 21 nucleotides, this means that each strand of the duplex is 21 nucleotides in length. Whilst it may be preferred that each strand of a double stranded siRNA is of the same length, this is not essential and each strand may be of separate defined length.

Thus, a STAT6 specific siRNA molecule having a specified length selected in accordance with the above may be prepared having an antisense strand which has a specified degree of complementarity to a selected part or fragment of the RNA molecule encoded by any one of SEQ ID No.'s 10, 12 or 14. The antisense strand may have substantial sequence complementarity (i.e. at least 70%, more preferably one of 80%, 85%, 90%, 95%, 97%, 98%, 99% or 100%) to a selected part or fragment of the RNA encoded by one of SEQ ID No's 10, 12 or 14, wherein that part or fragment has a length selected in accordance with this disclosure, and wherein that part or fragment has a contiguous sequence of nucleotides encoded by a corresponding part or fragment of one of SEQ ID Nos. 10, 12 or 14 and wherein the encoding part or fragment may start from any one of nucleotide positions:

1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3161, 3162, 3163, 3164, 3165, 3166, 3167, 3168, 3169, 3170, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, 3250, 3251, 3252, 3253, 3254, 3255, 3256, 3257, 3258, 3259, 3260, 3261, 3262, 3263, 3264, 3265, 3266, 3267, 3268, 3269, 3270, 3271, 3272, 3273, 3274, 3275, 3276, 3277, 3278, 3279, 3280, 3281, 3282, 3283, 3284, 3285, 3286, 3287, 3288, 3289, 3290, 3291, 3292, 3293, 3294, 3295, 3296, 3297, 3298, 3299, 3300, 3301, 3302, 3303, 3304, 3305, 3306, 3307, 3308, 3309, 3310, 3311, 3312, 3313, 3314, 3315, 3316, 3317, 3318, 3319, 3320, 3321, 3322, 3323, 3324, 3325, 3326, 3327, 3328, 3329, 3330, 3331, 3332, 3333, 3334, 3335, 3336, 3337, 3338, 3339, 3340, 3341, 3342, 3343, 3344, 3345, 3346, 3347, 3348, 3349, 3350, 3351, 3352, 3353, 3354, 3355, 3356, 3357, 3358, 3359, 3360, 3361, 3362, 3363, 3364, 3365, 3366, 3367, 3368, 3369, 3370, 3371, 3372, 3373, 3374, 3375, 3376, 3377, 3378, 3379, 3380, 3381, 3382, 3383, 3384, 3385, 3386, 3387, 3388, 3389, 3390, 3391, 3392, 3393, 3394, 3395, 3396, 3397, 3398, 3399, 3400, 3401, 3402, 3403, 3404, 3405, 3406, 3407, 3408, 3409, 3410, 3411, 3412, 3413, 3414, 3415, 3416, 3417, 3418, 3419, 3420, 3421, 3422, 3423, 3424, 3425, 3426, 3427, 3428, 3429, 3430, 3431, 3432, 3433, 3434, 3435, 3436, 3437, 3438, 3439, 3440, 3441, 3442, 3443, 3444, 3445, 3446, 3447, 3448, 3449, 3450, 3451, 3452, 3453, 3454, 3455, 3456, 3457, 3458, 3459, 3460, 3461, 3462, 3463, 3464, 3465, 3466, 3467, 3468, 3469, 3470, 3471, 3472, 3473, 3474, 3475, 3476, 3477, 3478, 3479, 3480, 3481, 3482, 3483, 3484, 3485, 3486, 3487, 3488, 3489, 3490, 3491, 3492, 3493, 3494, 3495, 3496, 3497, 3498, 3499, 3500, 3501, 3502, 3503, 3504, 3505, 3506, 3507, 3508, 3509, 3510, 3511, 3512, 3513, 3514, 3515, 3516, 3517, 3518, 3519, 3520, 3521, 3522, 3523, 3524, 3525, 3526, 3527, 3528, 3529, 3530, 3531, 3532, 3533, 3534, 3535, 3536, 3537, 3538, 3539, 3540, 3541, 3542, 3543, 3544, 3545, 3546, 3547, 3548, 3549, 3550, 3551, 3552, 3553, 3554, 3555, 3556, 3557, 3558, 3559, 3560, 3561, 3562, 3563, 3564, 3565, 3566, 3567, 3568, 3569, 3570, 3571, 3572, 3573, 3574, 3575, 3576, 3577, 3578, 3579, 3580, 3581, 3582, 3583, 3584, 3585, 3586, 3587, 3588, 3589, 3590, 3591, 3592, 3593, 3594, 3595, 3596, 3597, 3598, 3599, 3600, 3601, 3602, 3603, 3604, 3605, 3606, 3607, 3608, 3609, 3610, 3611, 3612, 3613, 3614, 3615, 3616, 3617, 3618, 3619, 3620, 3621, 3622, 3623, 3624, 3625, 3626, 3627, 3628, 3629, 3630, 3631, 3632, 3633, 3634, 3635, 3636, 3637, 3638, 3639, 3640, 3641, 3642, 3643, 3644, 3645, 3646, 3647, 3648, 3649, 3650, 3651, 3652, 3653, 3654, 3655, 3656, 3657, 3658, 3659, 3660, 3661, 3662, 3663, 3664, 3665, 3666, 3667, 3668, 3669, 3670, 3671, 3672, 3673, 3674, 3675, 3676, 3677, 3678, 3679, 3680, 3681, 3682, 3683, 3684, 3685, 3686, 3687, 3688, 3689, 3690, 3691, 3692, 3693, 3694, 3695, 3696, 3697, 3698, 3699, 3700, 3701, 3702, 3703, 3704, 3705, 3706, 3707, 3708, 3709, 3710, 3711, 3712, 3713, 3714, 3715, 3716, 3717, 3718, 3719, 3720, 3721, 3722, 3723, 3724, 3725, 3726, 3727, 3728, 3729, 3730, 3731, 3732, 3733, 3734, 3735, 3736, 3737, 3738, 3739, 3740, 3741, 3742, 3743, 3744, 3745, 3746, 3747, 3748, 3749, 3750, 3751, 3752, 3753, 3754, 3755, 3756, 3757, 3758, 3759, 3760, 3761, 3762, 3763, 3764, 3765, 3766, 3767, 3768, 3769, 3770, 3771, 3772, 3773, 3774, 3775, 3776, 3777, 3778, 3779, 3780, 3781, 3782, 3783, 3784, 3785, 3786, 3787, 3788, 3789, 3790, 3791, 3792, 3793, 3794, 3795, 3796, 3797, 3798, 3799, 3800, 3801, 3802, 3803, 3804, 3805, 3806, 3807, 3808, 3809, 3810, 3811, 3812, 3813, 3814, 3815, 3816, 3817, 3818, 3819, 3820, 3821, 3822, 3823, 3824, 3825, 3826, 3827, 3828, 3829, 3830, 3831, 3832, 3833, 3834, 3835, 3836, 3837, 3838, 3839, 3840, 3841, 3842, 3843, 3844, 3845, 3846, 3847, 3848, 3849, 3850, 3851, 3852, 3853, 3854, 3855, 3856, 3857, 3858, 3859, 3860, 3861, 3862, 3863, 3864, 3865, 3866, 3867, 3868, 3869, 3870, 3871, 3872, 3873, 3874, 3875, 3876, 3877, 3878, 3879, 3880, 3881, 3882, 3883, 3884, 3885, 3886, 3887, 3888, 3889, 3890, 3891, 3892, 3893, 3894, 3895, 3896, 3897, 3898, 3899, 3900, 3901, 3902, 3903, 3904, 3905, 3906, 3907, 3908, 3909, 3910, 3911, 3912, 3913, 3914, 3915, 3916, 3917, 3918, 3919, 3920, 3921, 3922, 3923, 3924, 3925, 3926, 3927, 3928, 3929, 3930, 3931, 3932, 3933, 3934, 3935, 3936, 3937, 3938, 3939, 3940, 3941, 3942, 3943, 3944, 3945, 3946, 3947, 3948, 3949, 3950, 3951, 3952, 3953, 3954, 3955, 3956, 3957, 3958, 3959, 3960, 3961, 3962, 3963, 3964, 3965, 3966, 3967, 3968, 3969, 3970, 3971, 3972, 3973, 3974, 3975, 3976, 3977, 3978, 3979, 3980, 3981, 3982 or 3983 in any one of SEQ ID Nos. 10, 12 or 14.

For example, SEQ ID No.1 represents the double stranded siRNA molecule, of strand length 21 nucleotides, having an antisense strand based on (and including) nucleotides 643-663 of SEQ ID No.10. SEQ ID No.2 represents the double stranded siRNA molecule having an antisense strand based on nucleotides 1903-1923 of SEQ ID No.10. SEQ ID No.3 represents the double stranded siRNA molecule having an antisense strand based on nucleotides 2399-2417 of SEQ ID No.10. SEQ ID No.4 represents the double stranded siRNA molecule having an antisense strand based on nucleotides 1277-1296 of SEQ ID No.10.

Accordingly, it is possible to prepare and utilise a wide variety of double stranded siRNA molecules, and each of these, together with their use in therapeutic methods for the treatment of respiratory tract allergic and/or non-allergic disease form part of the present invention.

Sense and Antisense Strands

In this specification, with respect to double stranded siRNA molecules, the following definitions apply to the terminology "sense" and "antisense".

A given double stranded siRNA molecule typically comprises two strands of RNA, each one being substantially complementary in sequence to the other such that they can bind together to form a duplex by Watson/Crick base pairing. The siRNA molecules of the invention may be designed for the purpose of enabling one strand of the duplex to bind to a target ribonucleic acid. In this specification the target ribonucleic acid is usually a STAT6 mRNA.

One strand of the siRNA duplex has substantial sequence complementarity (i.e. usually at least 70% complementarity) to a contiguous sequence of nucleotides forming part of the RNA sequence of the target mRNA. This strand of the siRNA duplex is designated the antisense strand and is complementary, or substantially complementary, to a part of the target mRNA to which the antisense strand is intended to bind as part of the mechanism of action of the siRNA.

The other strand of the duplex siRNA corresponds to and has substantial sequence identity (i.e. usually at least 70% identity) to a contiguous sequence of nucleotides forming part of the target mRNA sequence. This is designated the "sense" strand of the siRNA duplex.

Repression and Silencing

Ribonucleic acids of the invention are designed to repress or silence the expression of a target ribonucleic acid, peptide, polypeptide or protein or to repress a function of such ribonucleic acid, peptide, polypeptide or protein.

A repression of expression results in a decrease in the quantity of the target, preferably of a target protein, e.g. STAT6. For example, in a given cell the repression of a target (e.g. STAT6 protein) by administration of a ribonucleic acid of the invention results in a decrease in the quantity of the target relative to an untreated cell.

Repression of a function may be the decrease in transcription of an mRNA, or translation of a peptide or polypeptide.

Repression may be partial. Preferred degrees of repression are at least 50%, more preferably one of at least 60, 70, 80, 85 or 90%. A level of repression between 90% and 100% is considered a 'silencing' of expression or function.

Sequence Identity

Percentage (%) sequence identity is defined as the percentage of nucleic acid residues in a candidate sequence that are identical with residues in the given listed sequence (referred to by the SEQ ID No.) after aligning the sequences and introducing gaps if necessary, to achieve the maximum sequence identity. Sequence identity is preferably calculated over the entire length of the respective sequences.

Unless specified otherwise, where the aligned sequences are of different length, sequence identity of the shorter sequence is determined over the entire length of the longer sequence. For example, where a given sequence comprises 100 nucleotides and the candidate sequence comprises 10 nucleotides, the candidate sequence can only have a maximum identity of 10% to the entire length of the given sequence. This is further illustrated in the following examples:

| (A) | | |
|---|---|---|
| Given seq: | XXXXXXXXXXXXXXX | (15 nucleotides) |
| Comparison seq: | XXXXXYYYYYYY | (12 nucleotides) |

% sequence identity=the number of identically matching nucleotides after alignment divided by the total number of nucleotides in the given sequence, i.e. (5 divided by 15)× 100=33.3%

| (B) | | |
|---|---|---|
| Given seq: | XXXXXXXXXX | (10 nucleotides) |
| Comparison seq: | XXXXXYYYYYYZZYZ | (15 nucleotides) |

% sequence identity=number of identical nucleotides after alignment divided by total number of nucleotides in the given sequence, i.e. (5 divided by 10)×100=50%.

Alignment for purposes of determining percent nucleotide sequence identity can be achieved in various ways that are within the skill in the art.

Hybridisation Stringency

In accordance with the present invention, nucleic acids having an appropriate level of sequence identity may be identified by using hybridisation and washing conditions of appropriate stringency.

For example, RNA-RNA hybridisations may be performed according to hybridisation methods well known to a person of skill in the art, e.g. the method of Sambrook et al., ("Molecular Cloning, A Laboratory Manual, Cold Spring Harbor Laboratory Press, 2001).

Calculation of the melting temperature ($T_m$) at a given salt concentration is one method of determining hybridisation stringency. Nucleic acid duplexes of low sequence identity will have a lower $T_m$ than nucleic acid duplexes of higher sequence identity.

One of the most accurate derivations of the melting temperature is the nearest-neighbour method. This method is well known to persons of skill in the art, is suitable for calculating the $T_m$ of short nucleic acids and takes into account the actual sequence of the oligonucleotides as well as salt concentration and nucleic acid concentration.

The nearest-neighbour equation for both DNA and RNA based oligonucleotides is:

$$T_m = \left[\frac{[1000\Delta H°]}{A + \Delta S° + R\ln(C_t/4)}\right] - 273.15 + 16.6\log[Na^+]$$

where $\Delta H°$ (Kcal/mol) is the sum of the nearest-neighbour enthalpy changes for hybrids, A is a constant (−10.8) correcting for helix initiation, $\Delta S°$ is the sum of the nearest neighbour entropy changes, R is the Gas Constant (1.99 cal $K^{-1}mol^{-1}$) and $C_t$ is the molar concentration of the oligonucleotide. $\Delta H°$ and $\Delta S°$ values for both DNA and RNA nearest neighbour bases are publicly available (e.g. from Genosys Biotechnologies Inc.).

In general for RNA-RNA hybridisations under very high stringency conditions, the melting temperature of RNA duplexes of 100% sequence identity would be expected to be approximately greater than or equal to 60° C., although the actual $T_m$ for any given duplex requires empirical calculation.

Accordingly, nucleotide sequences can be categorised by an ability to hybridise under different hybridisation and washing stringency conditions which can be appropriately selected using the above equation or by other similar methods known to persons skilled in the art.

Sequences exhibiting 95-100% sequence identity are considered to hybridise under very high stringency conditions, sequences exhibiting 85-95% identity are considered to hybridise under high stringency conditions, sequences exhibiting 70-85% identity are considered to hybridise under intermediate stringency conditions, sequences exhibiting 60-70% identity are considered to hybridise under low stringency conditions and sequences exhibiting 50-60% identity are considered to hybridise under very low stringency conditions.

STAT6

In this specification, STAT6 may refer to any STAT6 nucleic acid, polypeptide, or to any homologue, mutant, derivative or fragment thereof.

In this specification, a STAT6 polypeptide or protein may be any peptide, polypeptide or protein having an amino acid sequence having a specified degree of sequence identity to one of SEQ ID Nos. 9, 11 or 13 or to a fragment of one of SEQ ID Nos. 9, 11 or 13 or to the peptide or polypeptide encoded by the nucleotide sequence of one of SEQ ID Nos. 10, 12 or 14 or a fragment of one of SEQ ID Nos. 10, 12 or 14. The specified degree of sequence identity may be from at least 60% to 100% sequence identity. More preferably, the specified degree of sequence identity may be one of at least 65%, 70%, 75%, 80%, 85%, 86%, 87%, 88%, 89%, 90%, 91%, 92%, 93%, 94%, 95%, 96%, 97%, 98% or 99% identity.

In this specification, a STAT6 nucleic acid may be any nucleic acid (DNA or RNA) having a nucleotide sequence having a specified degree of sequence identity to one of SEQ ID Nos. 10, 12 or 14, to an RNA transcript of any one of these sequences, to a fragment of any one of the preceding sequences or to the complementary sequence of any one of these sequences or fragments. Alternatively a STAT6 nucleic acid may be one that hybridises to one of these sequence under high or very high stringency conditions. The specified degree of sequence identity may be from at least 60% to 100% sequence identity. More preferably, the specified degree of sequence identity may be one of at least 65%, 70%, 75%, 80%, 85%, 86%, 87%, 88%, 89%, 90%, 91%, 92%, 93%, 94%, 95%, 96%, 97%, 98% or 99% identity.

The human STAT6 polypeptide and nucleotide sequence is available from the NCBI (http://www.ncbi.nlm.nih.gov/) database under accession number NM_003153 (GI: 23397677) (also see FIG. 4).

The mouse STAT6 polypeptide and nucleotide sequence is available from the NCBI (http://www.ncbi.nlm.nih.gov/) database under accession number NM_009284 (GI: 6678154) (also see FIG. 5).

The rat STAT6 polypeptide and nucleotide sequence is available from the NCBI (http://www.ncbi.nlm.nih.gov/) database under accession number XM_343223 (GI: 34865760) (also see FIG. 6).

A STAT6 nucleic acid may preferably refer to the nucleic acid encoding a human STAT6 polypeptide or protein or a homologue thereof.

Alternatively, STAT6 may refer to nucleic acid encoding a non-human STAT6 polypeptide or homologue thereof. A non-human STAT6 may preferably be selected from any one of a rat, mouse or other rodent (including any animal in the order Rodentia), and may also be selected from a pig, sheep, non-human primate or other non-human vertebrate organism or non-human mammal.

STAT6 homologues preferably have at least 60% sequence identity to the STAT6 sequence of the given organism. More preferably the level of sequence identity is at least 70, 80, 90 or 95%.

Fragments

A fragment may comprise a nucleotide or amino acid sequence encoding a portion of the corresponding full length sequence. In this specification the corresponding full length sequence may be one of SEQ ID Nos. 9 to 14. Said portion may be of defined length and may have a defined minimum and/or maximum length.

Accordingly, the fragment may comprise at least, i.e. have a minimum length of, 10, 11, 12, 13, 14, 15, 16, 17, 18, 19, 20, 25, 30, 40, 50, 60, 70, 80, 85, 90, 95, 96, 97, 98 or 99% of the corresponding full length sequence. The fragment may have a maximum length, i.e. be no longer than, 10, 11, 12, 13, 14, 15, 16, 17, 18, 19, 20, 25, 30, 40, 50, 60, 70, 80, 85, 90, 95, 96, 97, 98 or 99% of the corresponding full length sequence.

The fragment may comprise at least, i.e. have a minimum length of, 10 nucleotides or amino acids, more preferably at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 300, 400, 500, 600, 700, 800, 900, 1000, 1100, 1200, 1300, 1400, 1500, 1600, 1700, 1800, 1900 2000, 2100, 2200, 2300, 2400, 2500, 2600, 2700, 2800, 2900, 3000, 3100, 3200, 3300, 3400, 3500, 3600, 3700, 3800, 3900 or 4000 nucleotides or amino acids.

The fragment may have a maximum length of, i.e. be no longer than, 10 nucleotides or amino acids, more preferably no longer than 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 300, 400, 500, 600, 700, 800, 900, 1000, 1100, 1200, 1300, 1400, 1500, 1600, 1700, 1800, 1900 2000, 2100, 2200, 2300, 2400, 2500, 2600, 2700, 2800, 2900, 3000, 3100, 3200, 3300, 3400, 3500, 3600, 3700, 3800, 3900 or 4000 nucleotides or amino acids.

The fragment may have a length anywhere between the said minimum and maximum length.

The invention includes the combination of the aspects and preferred features described except where such a combination is clearly impermissible or expressly avoided.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

FIG. 1 Design of siRNA targeting STAT6.

Targeted DNA sequences (SEQ ID Nos. 15-18) encoding parts of the STAT6 mRNA and the corresponding duplex structure of the prepared siRNA (SEQ ID Nos. 1-4) are shown.

Figure 2:
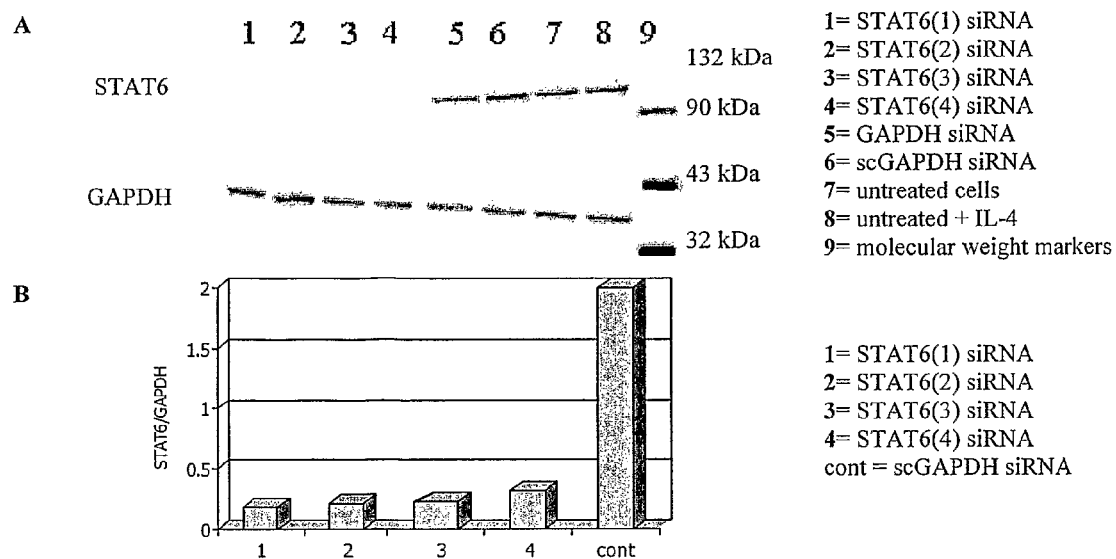

FIG. 2 Inhibition of STAT6 Expression by RNAi.

A549 cells were treated with individual siRNA at a final concentration of 100 nM.

(A). 60 hours after treatment cellular proteins were harvested, equal amounts (10 μg) separated by molecular weight using electrophoresis and immobilised onto synthetic membranes (Western Blotting). The presence of STAT6 protein (120 kDa) was then detected using a polyclonal anti-STAT6 antibody (Santa Cruz Biotechnology, Calif., USA) where the amount of STAT6 expression in each sample correlates with band density. Cells treated with STAT6(1) siRNA (SEQ ID No.1) had no detectable expression of STAT6 protein (no visible band). In lanes 2 & 3 (STAT6 (2) (SEQ ID No.2)-, STAT6(3) (SEQ ID No.3)-treated) STAT6 protein bands are barely detectable, indicating significant inhibition (>95%). STAT6(4) siRNA (SEQ ID No.4) was the least efficient although this siRNA still inhibited STAT6 expression by 90%. In contrast, control scrambled siRNA (scGAPDH, lane 6) had no effect on STAT6 expression. Similarly, STAT6 siRNA had no effect on GAPDH expression which is readily detectable as a 37 kDa protein band (using a GAPDH-specific antibody).

(B). STAT6 gene expression (mRNA production) in siRNA-treated cells was measured by real-time RT-PCR, allowing absolute quantification of gene expression. By comparing the amount of STAT6 expression to the housekeeping gene GAPDH (i.e. the ratio of STAT6/GAPDH expression: y-axis) the specific effects of siRNA can be measured. As shown, STAT6 siRNA (1-4) inhibit STAT6 mRNA by $\geq$90%. In contrast, cells treated with scGAPDH siRNA do not exhibit any reduction in STAT6 mRNA expression, indicating that the transfection procedure itself does not inhibit the STAT6 gene.

Figure 3:
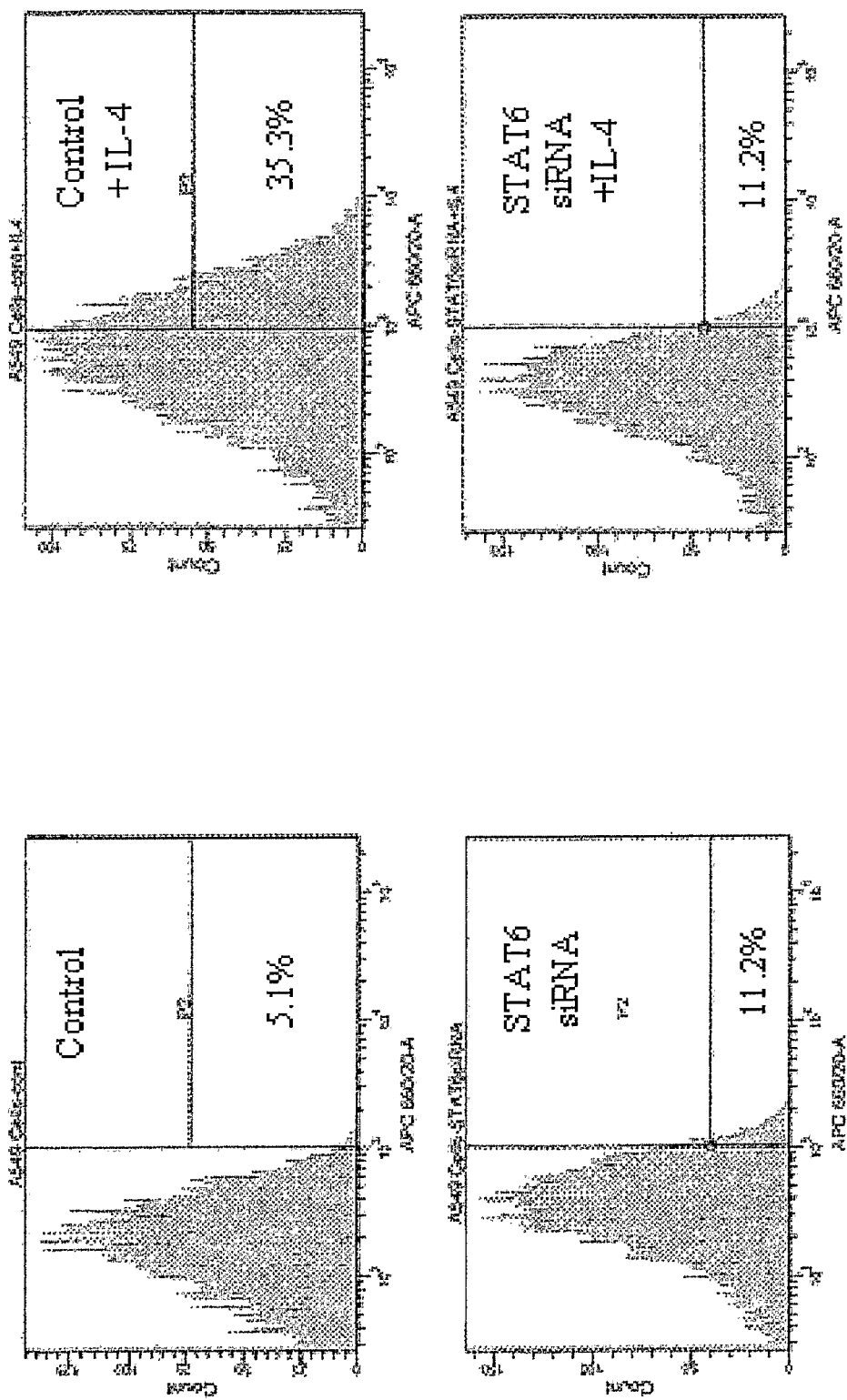

FIG. 3 RNAi of STAT6 leads to loss of STAT6 function.

To measure STAT6 activity A549 cells were cultured in the presence (right histogram) or absence (left histogram) of IL-4 (1 ng/ml) for 30 minutes prior to staining with anti-phospho-STAT6: Alexa fluor-647 labelled antibody (BD PharMingen, Oxford, UK). This antibody only recognises STAT6 molecules that are phosphorylated on tyrosine residue 641. After staining procedures, fluorescence in cells was measured by flow cytometry. In the histograms the amount of bound antibody is indicated by the relative amount of detectable fluorescence in individual cells (x-axis). The amount of fluorescence that is detectable above background levels is indicated in the gated region marked P2. As shown, IL-4 was capable of activating STAT6 in cells as indicated by the increase in fluorescence (top row, 35.3% versus 5.1% background in unstimulated cells). In contrast, when cells were treated with STAT6-specific siRNA, the ability of IL-4 to activate STAT6 was completely abolished (bottom row, 11.2% fluorescence in both stimulated and unstimulated cells)

FIG. 4. Extract from accession number NM003153 [gi: 23397677] in the NCBI database (http://www.ncbi.nlm.nih.gov/) showing amino acid sequence (SEQ ID No.9) and nucleotide sequence (SEQ ID No.10) for human STAT6.

FIG. 5. Extract from accession number NM009284 [gi: 6678154] in the NCBI database (http://www.ncbi.nlm.nih.gov/) showing amino acid sequence (SEQ ID No.11) and nucleotide sequence (SEQ ID No.12) for mouse STAT6.

FIG. 6. Extract from accession number XM343223 [gi: 34865760] in the NCBI database (http://www.ncbi.nlm.nih.gov/) showing amino acid sequence (SEQ ID No.13) and nucleotide sequence (SEQ ID No.14) for rat STAT6.

Figure 7:
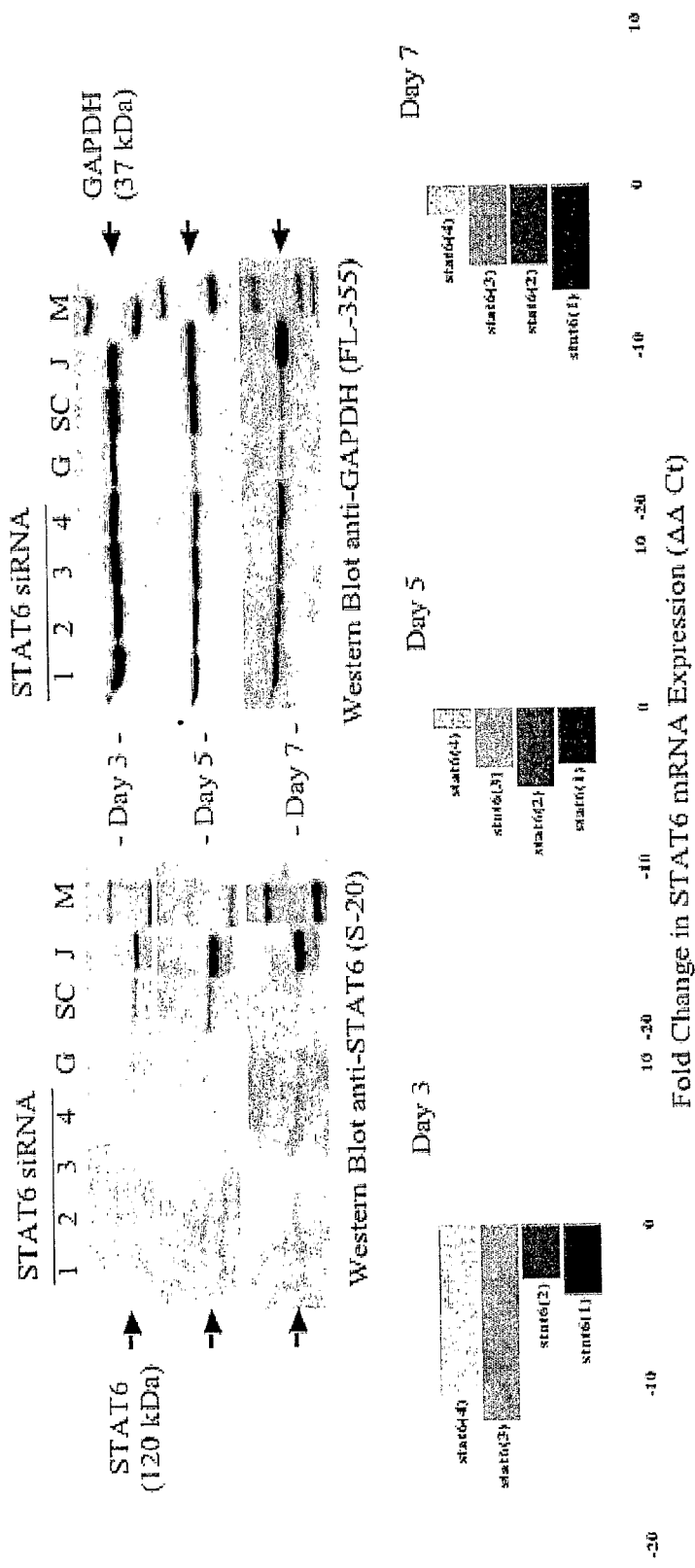

FIG. 7. Inhibition of STAT6 expression in human lung epithelial cells by RNAi persists for several days.

(G=GAPDH siRNA, J=Jurkatt cell lysate, M=size markers, all lanes=10 µg of protein, blots are representative of at least 3 individual experiments).

Figure 8:
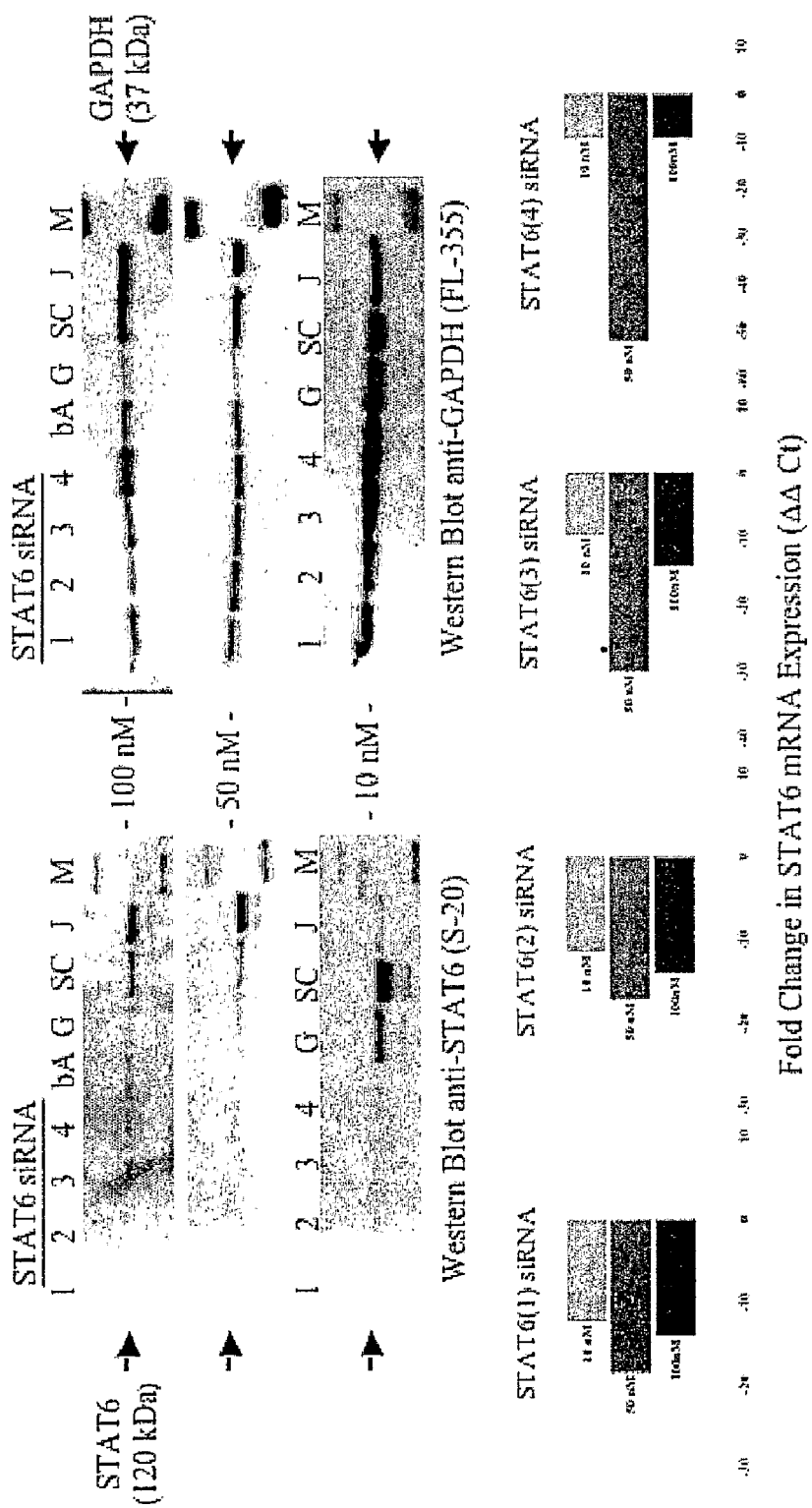

FIG. 8. STAT6 siRNA are efficient at concentrations as low as 10 nM. (G=GAPDH siRNA, bA=b-actin siRNA, J=Jurkatt cell lysate, M=size markers, all lanes=10 µg of protein, results representative of 3 independent experiments).

Figure 9:
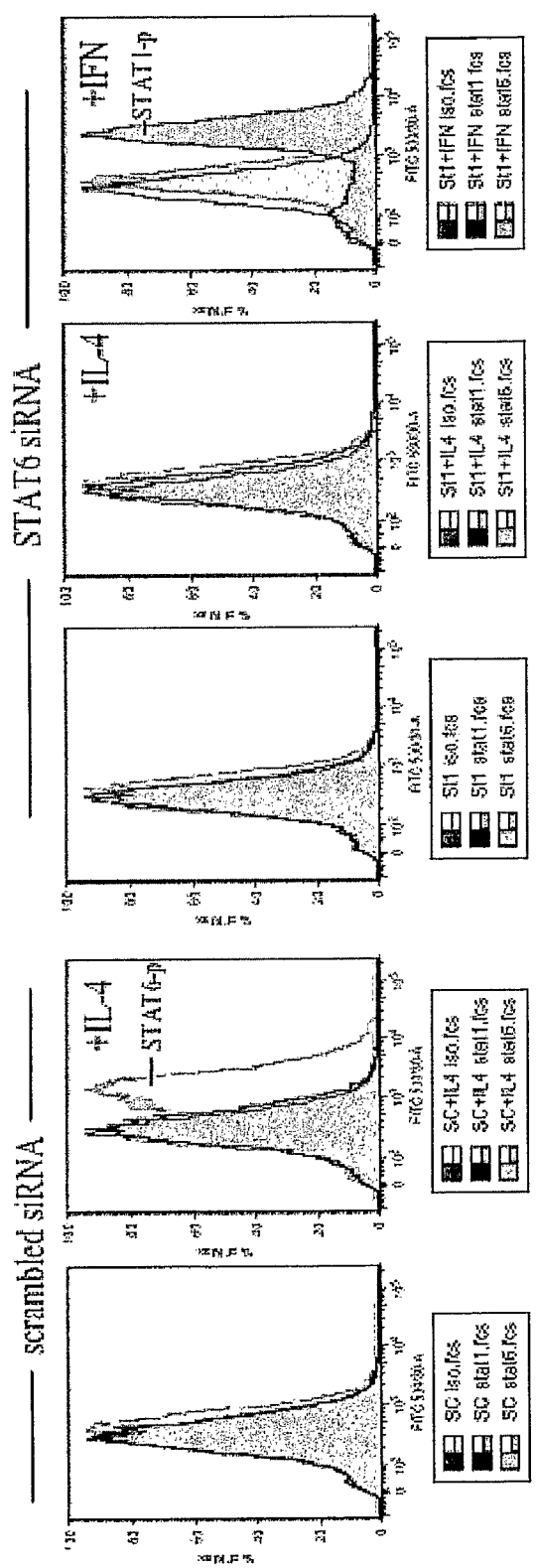

FIG. 9. RNAi abolishes expression of functional STAT6 protein without inducing an interferon response.

Figure 10:
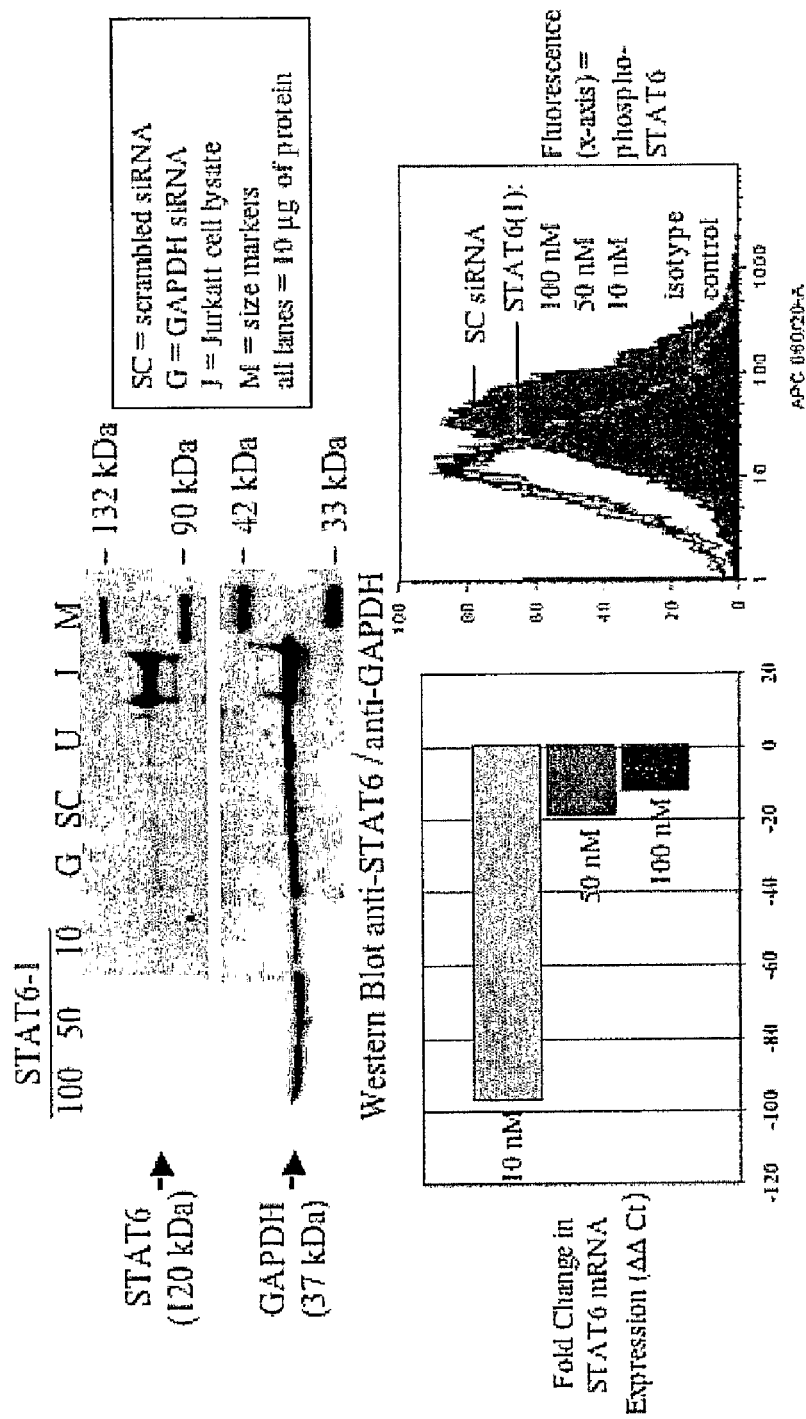

FIG. 10. STAT6 suppression by RNAi is readily achievable in diverse human lung cell types.

Figure 11:
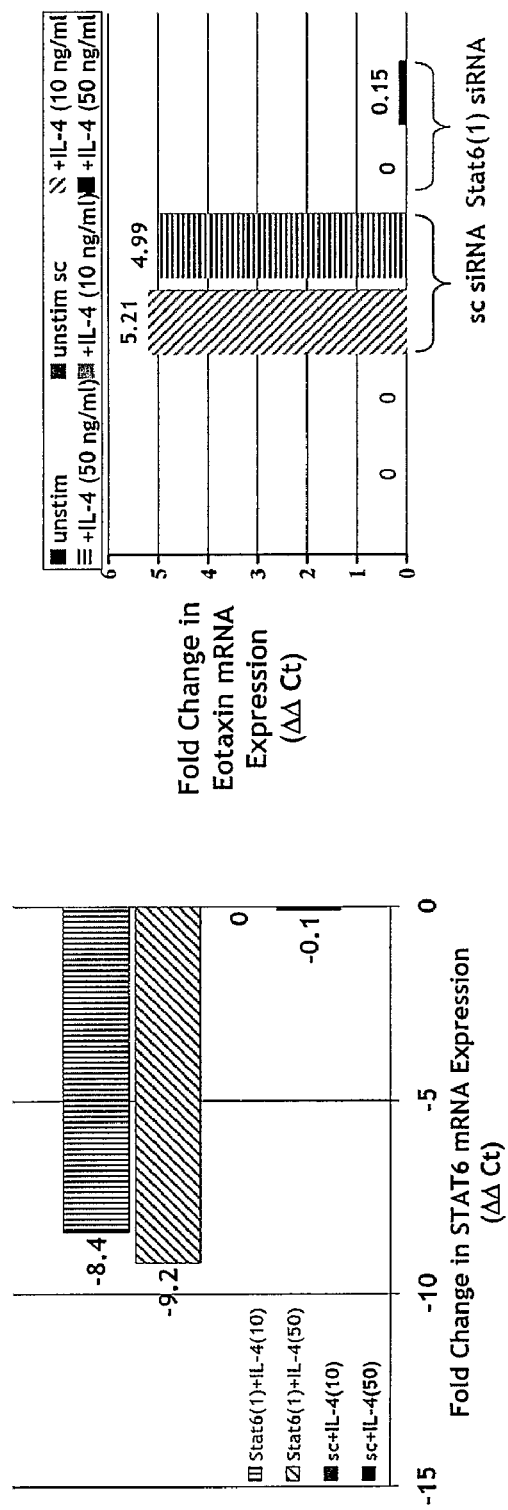

FIG. 11. RNAi of STAT6 abolishes the ability of IL-4 to up-regulate eotaxin-1 mRNA expression in human lung epithelial cells.

DETAILED DESCRIPTION OF THE BEST MODE OF THE INVENTION

Specific details of the best mode contemplated by the inventors for carrying out the invention are set forth below, by way of example. It will be apparent to one skilled in the art that the present invention may be practiced without limitation to these specific details.

STAT6 siRNA

Sequences within the coding region of STAT6 mRNA (GenBank, U16031) only were selected for targeting by siRNA. Regions near the start codon (within 75 bases) were avoided as they may contain regulatory protein binding sites.

To ensure specificity, selected target sites were compared by BLAST® (NCBI) search for homology with other known coding sequences. Target sequences were also selected on the basis of having a GC content <40% and beginning with AA to allow thymidine overhangs (tt) in the subsequent siRNA (FIG. 1).

Pure STAT6 siRNA duplexes were chemically synthesised according to the inventors design by Ambion Inc. (Austin, Tex., USA) and supplied as dried RNA oligonucleotide. Reconstituted siRNA were subsequently employed in cell treatment experiments.

Targeting of STAT6 Gene Expression by STAT6 siRNA

STAT6-expressing lung epithelial cells (A549) were treated with individual STAT6 siRNA and their ability to subsequently inhibit STAT6 expression determined by measuring both STAT6 mRNA and STAT6 protein expression (FIG. 2). To ensure efficient cellular targeting, siRNA were complexed with a commercially available cationic lipid reagent (Lipofectamine™, Invitrogen) and transfected into cells.

STAT6 siRNA were validated against commercially available GAPDH ('housekeeping' gene) siRNA and scrambled GAPDH siRNA with no known homology to human mRNA sequences (Ambion, Inc.) i.e. positive and negative controls respectively. In these experiments STAT6 siRNA duplexes were shown to inhibit the expression of both STAT6 mRNA and STAT6 protein expression in treated cells. Furthermore, this suppression was STAT6-specific in that the expression of non-related housekeeping genes such as GAPDH, were not affected.

STAT6 Function is Abolished by STAT6 siRNA Treatment

In order for RNAi to be a successful therapeutic it is essential that the targeting of genes leads to loss of protein function within treated cells. Therefore, in addition to measuring STAT6 expression (as shown above), we determined the effects of siRNA treatment on STAT6 activity within cells. As STAT6 protein has to become phosphorylated within cells in order for it to mediate its effects, we employed an assay that directly measures the amount of phosphorylated STAT6 within intact cells. This assay utilises an anti-phospho-STAT6 antibody (BD-PharMingen) that fluorescently labels cells expressing the phosphorylated STAT6 protein. The amount of detectable fluorescence in IL-4 treated cells (measured by flow cytometry) is directly related to the amount of phosphorylated STAT6 (FIG. 3).

To activate STAT6, cells were stimulated with interleukin-4 (IL-4), a chemical messenger that is produced during allergic responses and naturally activates STAT6 in cells. Using this as say we were able to unequivocally demonstrate that RNAi of STAT6 leads to elimination of STAT6 function (phosphorylation) in cells.

A 90% inhibition of gene expression does not necessarily correlate with complete loss of STAT6 protein expression and therefore by extrapolation, its function within cells. Accordingly, the antibody staining experiments (flow cytometry—FIG. 3) were performed. These results show that STAT6 siRNA treatment leads to loss of STAT6 function. STAT6 protein expression was inhibited following siRNA treatment (as demonstrated by Western Blotting) and this deficiency appears to be absolute in that STAT6-phosphorylation in response to interleukin-4 stimulation could not be detected by flow cytometry.

Inhibition of STAT6 Expression in Human Lung Epithelial Cells by RNAi Persists for Several Days Referring to the results set out in FIG. 7. A549 cells were transfected with 100 nM STAT6 siRNA 1-4 (SEQ ID No.s 1-4) on day 0. Protein and RNA fractions were prepared from cells harvested on day 3, day 5 & day 7 post-transfection and analysed for STAT6 protein/mRNA expression by Western blotting (FIG. 7—top panels) and real-time RT-PCR respectively. On day 3, STAT6 protein expression was completely abolished by STAT6 siRNA treatment (GAPDH levels were unaltered). In contrast, scrambled siRNA (SC) did not inhibit STAT6 (or GAPDH) protein expression. The same effect was discernable on day 5 and day 7. Some recovery was detectable on day 7 after siRNA-4 treatment (FIG. 7—left blot).

RT-PCR analysis using human STAT6-specific primers confirmed STAT6 inhibition (normalised fold change relative to treatment with SC siRNA, ΔΔCt), STAT6 mRNA expression was significantly suppressed at all time points post-treatment.

STAT6 siRNA are Efficient at Concentrations as Low as 10 nM

To test the efficacy of STAT6 RNAi, A549 lung epithelial cells were transfected with various concentrations of individual STAT6 siRNA 1-4 (SEQ ID Nos. 1-4). The results are set out in FIG. 8. Cells were harvested on day 3 post-transfection and protein and RNA fractions subject to analysis for STAT6 protein/mRNA expression by Western blotting (FIG. 8—top panel) and real-time RT-PCR respectively.

STAT6 siRNA were shown to inhibit STAT6 expression at all concentrations tested, whereas scrambled (SC) siRNA had no effect on STAT6 expression (GAPDH levels were unaffected by either treatment). RT-PCR analysis showed 50 nM to be the most potent siRNA concentration in terms of STAT6 mRNA inhibition (fold change, ΔΔCt) and this was confirmed at the protein level by Western blotting. However, even with 10 nM siRNA (equivalent to 0.13 ng/ml of dsRNA) there was significant suppression of STAT6 expression.

STAT6 siRNA-1 (SEQ ID No.1) and STAT6 siRNA-3 (SEQ ID No.3) completely inhibited STAT6 protein expression at 10 nM. STAT6 siRNA-2 (SEQ ID No.2) and STAT6-4

(SEQ ID No.4) showed weaker inhibition at the 10 nM concentration (faint bands are observable on the Western blot).

RNAi Abolishes Expression of Functional STAT6 Protein Without Inducing an Interferon Response Human lung epithelial cells (A549) were transfected with either 20 nM STAT6 siRNA-1 (SEQ ID No.1) (3 right panels) or with 20 nM scrambled (SC) siRNA that is non-homologous with any known human gene (mRNA). 3 days post-transfection, cells were stimulated with 100 ng/ml of human rIL-4 for 60 minutes, then harvested, fixed and stained for intracellular expression of phosphorylated-STAT6 using Alexa-Fluor-488 conjugated anti-human phospho-STAT6 (BD PharMingen). As dsRNA (including some siRNA) have been reported to activate an interferon response in certain human cell types, cells were also stained for STAT1-phosphorylation (STAT1 is specifically phosphorylated by interferon-receptor signalling) using a phospho-STAT1-specific antibody (BD-PharMingen).

The results are set out in FIG. 9. In the absence of IL-4 stimulation, SC-siRNA-treated cells did not exhibit any detectable STAT6 phosphorylation (FIG. 9—left panel) when compared with isotype control stained cells. In contrast, IL-4 was able to readily induce STAT6 phosphorylation (Alex-Fluor-488 fluorescence) in SC-siRNA treated cells. When cells were treated with STAT6-1 siRNA this ability of IL-4 to phosphorylate STAT6 was abolished as indicated by the absence of fluorescent staining—indicating an absence of functional STAT6 protein in STAT6 siRNA-1 (SEQ ID No.1) treated cells. Intracellular staining with anti-phospho-STAT1 showed a complete absence of STAT1-phosphorylation in siRNA-treated cells (SC or STAT6-1), indicating that interferon signalling was not induced by siRNA-treatment (this is in agreement with inventors RT-PCR data showing that the interferon-response gene OAS-1 is not modulated upon siRNA-treatment).

To confirm interferon-responsiveness, parallel siRNA-treated epithelial cell cultures were stimulated with exogenous human rIFN-γ (10 ng/ml for 60 minutes). Under these conditions, STAT1-phosphorylation was readily detectable by specific antibody staining (FIG. 9—right panel).

The combined results from these studies show that functional STAT6 protein expression is readily and specifically abolished in epithelial cells by 20 nM STAT6 siRNA and that siRNA treatment does not induce detectable interferon responses in targeted cells. Data is representative of at least 5 independent experiments.

STAT6 Suppression by RNAi is Readily Achievable in Diverse Human Lung Cell Types HL cells (lung fibroblasts) were transfected with various concentrations of STAT6 siRNA-1 (SEQ ID No.1) and cells harvested on day 3 post-transfection were analysed for STAT6 expression by Western blotting, real-time RT-PCR & flow cytometric analysis. The results are set out in FIG. 10.

Similar to epithelial cells, STAT6 protein expression in fibroblasts was completely and specifically abolished by STAT6 siRNA-1 (SEQ ID No.1) treatment (GAPDH levels were unaltered). 100 nM, 50 nM & 10 nM STAT6 siRNA-1 (SEQ ID No.1) all inhibited STAT6 protein expression by day 3 post-transfection (FIG. 10—top panel). In contrast, scrambled siRNA (SC) did not modulate STAT6 or GAPDH protein expression. RT-PCR analysis confirmed STAT6 inhibition in that relative to SC/housekeeping controls (ΔΔCt), STAT6 mRNA expression was significantly suppressed at all siRNA concentrations.

In this cell type, 10 nM STAT6-1 siRNA mediated the greatest inhibition of STAT6 mRNA levels (normalised mean fold change in STAT6 mRNA expression relative to treatment with SC siRNA=−97). To further confirm knockdown, siRNA-treated cells were stimulated with 100 ng/ml of human rIL-4 for 60 minutes and STAT6-phosphorylation measured by flow cytometric analysis (lower-right panel). Using a phospho-STAT6-specific antibody (BD-PharMingen), STAT6-phosphorylation was shown to be completely abolished in STAT6 siRNA-1 (SEQ ID No.1)-treated/IL-4 stimulated cells at all concentrations of STAT6 siRNA-1 (SEQ ID No.1), indicating an absence of functional STAT6 protein in these cells. In contrast, SC siRNA (100 nM) did not inhibit the ability of IL-4 to phosphorylate STAT6 in HL cells (indicated by relative increase in fluorescence).

RNAi of STAT6 Abolishes the Ability of IL-4 to Up-Regulate Eotaxin-1 mRNA Expression in Human Lung Epithelial Cells.

To further confirm functional STAT6 blockade, the ability of IL-4 to drive the expression of a known STAT6-responsive gene (eotaxin-1) in STAT6 siRNA-treated cells was determined. The results are shown in FIG. 11.

Lung epithelial cells (A549) were transfected with STAT6-1 siRNA (SEQ ID No.1) or scrambled SC siRNA (20 nM final concentration) and 3 days post-transfection were treated with human rIL-4 (10, 50 ng/ml) for a further 12 hours. Total RNA was then extracted from harvested cells and STAT6/eotaxin-1 mRNA expression determined by real-time RT-PCR.

As illustrated in FIG. 11 (left panel), STAT6 mRNA expression was significantly inhibited by STAT6-1 siRNA (SEQ ID No.1) treatment (relative fold change, ΔΔCt). In contrast SC siRNA had no effect on relative levels of STAT6 mRNA. When eotaxin-1 mRNA transcript levels were determined in the same samples using human eotaxin-1 specific primers (FIG. 11—right panel), IL-4 was shown to up-regulate the relative levels of eotaxin-1 mRNA levels in SC-siRNA-treated cells (ΔΔCt relative to unstimulated cells). In contrast, IL-4 did not significantly modulate eotaxin-1 mRNA expression in STAT6-1 siRNA (SEQ ID No.1)-treated cells.

Although these findings are preliminary and require validation at the protein level, they indicate that IL-4 induced regulation of eotaxin-1 gene expression in human lung epithelial cells is STAT6-dependent and confirm independent findings in mice and humans that eotaxin-1 is a STAT6-regulated gene.

These findings also illustrate the utility of STAT6 RNAi as a tool for investigating human STAT6 function and, given the reported importance of the IL-4-STAT6-eotaxin axis in allergic asthma, indicate the potential therapeutic benefit of inhibiting this pathway in vivo.

Discussion

The results described show that by designing siRNA specific to STAT6 effective inhibition of STAT6 gene (mRNA) and protein expression can be achieved in cell types that are relevant to asthma. Importantly, the results also demonstrate that treatment of cells with STAT6 siRNA leads to the abolition of STAT6 function upon stimulation with physiological stimuli.

The results show that STAT6 directed siRNA are active in successfully repressing the cellular expression and activity of STAT6 at very low concentrations, e.g. down to 10 nM. Prior art antisense techniques, which proved unsuccessful, required much higher concentrations of antisense DNA, often up to 100 times higher. The efficacy of low concentrations of STAT6 directed siRNA demonstrated here provides a significant improvement over the prior art. In particular, therapeutic efficacy at such low concentration alleviates many of the problems of delivery of high concentrations of active agent which remain in the cell without undergoing degradation for sufficient time for them to take effect.

As STAT6 is known to be a central mediator of many of the dysregulated processes that take place in allergic disease of the respiratory tract, the targeting of this gene by this approach provides a route of unique therapy for diseases including asthma, rhinitis and non-allergic asthma where STAT6 has also been implicated.

Accordingly, a STAT6 siRNA based treatment for respiratory tract allergic disease is provided which, in the case of asthma or rhinitis, may operate by selectively down-regulating STAT6 expression, ameliorating the allergic inflammation-inducing effects of STAT6 in patients.

REFERENCES

1. Barnes, P. J. & Hansel, T. T. The need for new therapy. *New Drugs for Asthma, Allergy and COPD. Prog. Respir. Res.* (Karger) 31, 2-5 (2001).
2. Izuhara, K., Shirakawa, T., Adra, C. N., Hamasaki, N. & Hopkin, J. M. Emerging therapeutic targets in allergy: IL-4Ra and Stat6. *Emerging Therapeutic Targets* 3, 381-389 (1999).
3. Caplen, N. J. A new approach to the inhibition of gene expression. *Trends Biotech.* 20, 49-51 (2002).
4. Elbashir, S. M. et al. Duplexes of 21-nucleotide RNAs mediate RNA interference in cultured mammalian cells. *Nature* 411, 494-498 (2001).
5. Elbashir, S. M. et al. Duplexes of 21-nucleotide RNAs mediate RNA interference in cultured mammalian cells. *Nature* 411, 494-498 (2001).
6. Foster, P. S. STAT6: an intracellular target for the inhibition of allergic disease. *Clin. Exp. Allergy* 29, 12-16 (1999).
7. Izuhara, K., Shirakawa, T., Adra, C. N., Hamasaki, N. & Hopkin, J. M. Emerging therapeutic targets in allergy: IL-4Ra and Stat6. *Emerging Therapeutic Targets* 3, 381-389 (1999).
8. Bertrand, J-R et al. Comparison of antisense oligonucleotides and siRNAs in cell culture and in vivo. *Biochemical and Biophysical Research Communications* 296 (2002) 1000-1004.
9. Bitko, V et al. Inhibition of respiratory viruses by nasally administered siRNA. *Nature Medicine* Vol 11 No. 1 January 2005 50-55.
10. Soutschek, J et al. Therapeutic silencing of an endogenous gene by systematic administration of modified siRNAs. *Nature* Vol 432, 11 Nov. 2004 173-178.
11. Sioud, M et al. Cationic liposome-mediated delivery of siRNAs in adult mice. *Biochemical and Biophysical Research Communications* 312 (2003) 1220-1225.
12. Massaro, D et al. Noninvasive delivery of small inhibitory RNA and other reagents to pulmonary alveoli in mice. *Am J Physiol Lung Cell Mol Physiol* L1066-L1070, 2 Jul. 2004.
13. Stolzenberger, S et al. Specific inhibition of interleukin-4-dependent Stat6 activation by an intracellularly delivered peptide. *Eur J Biochem* 268 4809-4814 (2001).
14. Popescu, F-D. New asthma drugs acting on gene expression. *J Cell Mol Med* Vol 7 No. 4 2003 475-486.
15. WO 98/40478.
16. Danahay, H; Hill, S; Owen, C. E. (2000). The in vitro and in vivo pharmacology of antisense oligonucleotides targeted to murine STAT6. Inflamm. Res. 49: 692-699.

The invention claimed is:

1. A therapeutically active isolated double-stranded short interfering ribonucleic acid (siRNA) consisting essentially of a sense strand having a nucleotide sequence length of 18 to 23 nucleotides and an antisense strand having a nucleotide sequence length of 18 to 23 nucleotides said nucleotide sequence of said sense strand has a sequence identity of at least 80% to that of a contiguous nucleotide sequence of length 18 to 23 nucleotides which is contained in the messenger RNA (mRNA) sequence encoded by one of the human, mouse and rat STAT6 nucleotide sequences defined herein respectively as SEQ ID No 10, SEQ ID No 12 and SEQ ID No 14; and said nucleotide sequence of said antisense strand having a sequence complementarity of at least 80% to that of a contiguous nucleotide sequence of length 18 to 23 nucleotides which is contained in one of the RNA sequences encoded by one of the human, mouse and rat STAT6 nucleotide sequences defined herein respectively as SEQ ID No 10, SEQ ID No 12 and SEQ ID No 14, at least one of said sense strand and said antisense strand having a sequence identity of at least 80% to the corresponding strand of SEQ ID No 1, whereby said siRNA has the property of at least repressing expression of STAT6 mRNA and protein in vitro.

2. A double-stranded siRNA capable of at least repressing expression of STAT6 mRNA and protein in vitro, said siRNA having a sense strand with a sequence identity of at least 80% to the corresponding strand of SEQ ID No 1.

3. A double-stranded siRNA capable of at least repressing expression of STAT6 mRNA and protein in vitro, said siRNA having an antisense strand with a sequence identity of at least 80% to the corresponding strand of SEQ ID No 1.

4. A double-stranded siRNA comprising SEQ ID No. 1.

5. A pharmaceutical composition comprising a double-stranded siRNA as claimed in claim 1, the composition being formulated for the treatment of an allergic disease or a disease of the respiratory tract and further comprising a pharmaceutically acceptable diluent, carrier or adjuvant.

6. A pharmaceutical composition comprising a double-stranded siRNA as claimed in claim 2, the composition being formulated for the treatment of an allergic disease or a disease of the respiratory tract and further comprising a pharmaceutically acceptable diluent, carrier or adjuvant.

7. A pharmaceutical composition comprising a double-stranded siRNA as claimed in claim 3, the composition being formulated for the treatment of an allergic disease or a disease of the respiratory tract and further comprising a pharmaceutically acceptable diluent, carrier or adjuvant.

8. A pharmaceutical composition comprising a double-stranded siRNA as claimed in claim 4, the composition being formulated for the treatment of an allergic disease or a disease of the respiratory tract and further comprising a pharmaceutically acceptable diluent, carrier or adjuvant.

9. An siRNA according to claim 1, wherein the sense and antisense strands are of the same length.

10. An siRNA according to claim 1, wherein each said strand has a length of 19, 20, 21 or 22 nucleotides.

11. A pharmaceutical composition as claimed in claim 6, which is formulated for oral or nasal administration.

12. A pharmaceutical composition as claimed in claim 6, wherein said carrier is a lipophilic carrier or vesicle.

13. A method of treating an allergic disease in a patient in need of such treatment, which comprises administering to the patient an siRNA as claimed in claim 1.

14. A method of treating an allergic disease in a patient in need of such treatment, which comprises administration to the patient of a pharmaceutical composition according to claim 6.

15. A method according to claim 14, in which the administration is oral, inhalational or nasal.

16. A method of treating a disease in a patient in need of such treatment, which comprises administering to the patient an siRNA according to claim 4 or a pharmaceutical formulation according to claim 6 wherein said disease is selected from the group consisting of asthma, non-atopic asthma and rhinitis.

* * * * *